US005635371A

United States Patent [19]
Stout et al.

[11] Patent Number: 5,635,371
[45] Date of Patent: Jun. 3, 1997

[54] CHEMICAL METHOD FOR SELECTIVE MODIFICATION OF THE N- AND/OR C-TERMINAL AMINO ACID α-CARBON REACTIVE GROUP OF A RECOMBINANT POLYPEPTIDE OR A PORTION THEREOF

[75] Inventors: Jay Stout, Lincoln; Fred W. Wagner, Walton, both of Nebr.; Thomas R. Coolidge, Falls Village, Conn.; Bart Holmquist, Waltham, Mass.

[73] Assignee: BioNebraska, Inc., Lincoln, Nebr.

[21] Appl. No.: 294,434

[22] Filed: Aug. 23, 1994

Related U.S. Application Data

[63] Continuation of Ser. No. 912,798, Jul. 13, 1992, abandoned.

[51] Int. Cl.$^6$ .................................................. C12P 21/00
[52] U.S. Cl. .................................... 435/69.1; 435/172.3
[58] Field of Search ............................. 435/69.1, 172.3

[56] References Cited

U.S. PATENT DOCUMENTS

| 4,431,739 | 2/1984 | Riggs | 435/69.1 |
|---|---|---|---|
| 4,801,536 | 1/1989 | Stahl et al. . | |
| 4,810,777 | 3/1989 | Zasloff . | |
| 5,004,686 | 4/1991 | Cohen et al. | 435/69.1 |
| 5,045,531 | 9/1991 | Berkowitz et al. . | |
| 5,137,872 | 8/1992 | Seely et al. | 530/324 |
| 5,166,321 | 11/1992 | Lai et al. | 435/69.1 |

FOREIGN PATENT DOCUMENTS

| A-53274/90 | 10/1990 | Australia . |
|---|---|---|
| 0197794 | 10/1986 | European Pat. Off. . |
| 0458475A2 | 11/1991 | European Pat. Off. . |
| 2246133 | 1/1992 | United Kingdom . |
| 86/02077 | 4/1986 | WIPO . |
| WO8802406 | 4/1988 | WIPO . |
| WO88/07085 | 9/1988 | WIPO . |
| WO88/07086 | 9/1988 | WIPO . |
| WO91/08190 | 6/1991 | WIPO . |
| WO91/19737 | 12/1991 | WIPO . |

OTHER PUBLICATIONS

Schellenberger et al., "Proteinase–catalyzed conversion of a substance P–precursor peptide," *Int. J. Peptide Protein Res.*, 39, 1992, pp. 472–476.

Schellenberger et al., "Peptide production by a combination of gene expression, chemical syntheses, and protease–catalyzed conversion," *Int. J. Peptide Protein Res.*, 41, 1993, pp. 326–332.

Morihara, "Using proteases in peptide syntheses," *TibTech*, vol. 5, Jun. 1987, pp. 164–170.

Carles et al., "C–terminal labelling of β–casein," *FEBS Letters*, vol. 212, No. 1, Feb. 1987, pp. 163–167.

Bongers et al., "Comparison of enzymatic semisyntheses of peptide amides: human growth hormone releasing factor and analogs," *Biomed. Biochim. Acta*, Acta, 50 1991, pp. S157–S162.

Bongers et al., "Semisynthesis of human growth hormone–releasing factor by trypsin catalyzed coupling of leucine amide to a C–terminal acid precursor," *Int. J. Peptide Protein Res.*, 40, 1992, pp. 268–273.

Fruton, "Proteinase–catalyzed synthesis of peptide bonds," *Advances in Enzymology*, vol. 53, A. Meister, Ed., 1982, pp. 239–306.

Cha et al., *Biochemical Pharm.*, 30, 1981, pp. 1507–1515.

Kempe et al., *Biotechnology*, 4, 1992, pp. 565–568.

Shen, *Proc. Natl. Acad. Sci. USA*, 81, 1984, pp. 4627–4631.

*Science*, vol. 177, 18 Aug. 1972, Lancaster, PA, US, pp. 623–626, M.A. Ruttenberg, "Human Insulin: Facile Synthesis by Modification of Porcine Insulin".

*Hoppe–Seyler's Zeitschrift Fur Physiologischen Chemie*, vol. 357, Jun. 1976, Berlin D., pp. 759–767, R. Obermeir and R. Geiger, "A New Semisynthesis of Human Insulin".

Agarwal et al., *Biochemical Pharm.*, 26, 354–367 (1977).

R. Barker, *Methods Enzymol.*, 34, 317–328 (1974).

R. Bateman et al., *J. Biol. Chem.*, 260, pp. 9088–9091 (1985).

S. Beaucage et al., *Tetra. Letters*, 221:859 (1981).

G.S. Bethell et al., *J. Biol. Chem.*, 254, 2572–2574 (1979).

Cha et al., *Biochemical Pharm.*, 24, 2187–2197 (1975).

Degrado et al., *J. of Cellular Biochem.*, 29, 83–93 (1985).

J. Engels, *Protein Engineering*, 1:195–199 (1987).

Hanada et al., *J. Biol. Chem.*, 263:7181 (1988).

J. Johansen, *Carlsberg Res. Commun.*, 41, 73 (1976).

K. Itakura et al., *Science*, 198:1056 (1977).

(List continued on next page.)

*Primary Examiner*—Charles L. Patterson, Jr.
*Attorney, Agent, or Firm*—Merchant, Gould, Smith, Edell, Welter & Schmidt

[57] ABSTRACT

The invention provides for a chemical method for preparing a recombinant single copy polypeptide or a portion thereof with a modified terminal amino acid α-carbon reactive group selected from the group consisting of N-terminal α-amine, C-terminal α-carboxyl, and a combination thereof. The steps of the method involve forming the recombinant single copy polypeptide or a portion thereof so that the single copy polypeptide is protected with one or more biologically added protecting groups at the N-terminal α-amine, C-terminal α-carboxyl. The recombinant single copy polypeptide can then be reacted with up to three chemical protecting agents to selectively protect reactive side chain groups and thereby prevent side chain groups from being modified. The recombinant single copy polypeptide can be cleaved with at least one cleavage reagent specific for the biological protecting group to form an unprotected terminal amino acid α-carbon reactive group. The unprotected terminal amino acid α-carbon reactive group is modified with at least one chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of a recombinantly produced polypeptide.

17 Claims, No Drawings

OTHER PUBLICATIONS

*Kirk–Othmer Encyclopedia of Chemical Technology*, 4th Edition, vol. 12, pp. 603–617 (1991).
B. Lewin, *Genes*, 4th Edition, pp. 606–608, Oxford Press, New York, NY (1990).
Li et al., *PNAS*, 80, 2216 (1983).
S. Marcus, *Methods Enzymol.*, 34, 377–385 (1974).
I. Matsumoto, *Methods Enzymol.*, 34, 329–341 (1974).
A. Matsuura et al., *Methods Enzymol.*, 34, 303–4 (1974).
B. Nilsson et al., *EMBO Journal*, 4:1075 (1985).
J. Pierce et al., *Biochem.*, 19:934–942 (1980).
Ray et al., 201st ACS National Meeting, Atlanta, GA, *Abstract Papers Am. Chem.* Soc. 201, Abstract Biot. 48 (1991).
W. Scouten, *Methods Enzymol.*, 34, 288–294 (1974).
Spindel et al., *PNAS*, 81, 5699 (1984).
Sutton et al., *BBRC*, 134, 386–392 (1986).
Tajima et al., *J. Fermentation & Bioengineering*, 72:362 (1991).
Taylor, P.W. et al., *Biochemistry*, 9, 2638 (1970).
Williams et al., *Biochemical Pharm.*, 29, 589–595 (1980).
Yoo et al., *J. Biol. Chem.*, 264:17078 (1989).
Bodanszky (1988) Peptide Chemistry, pp. 1–9 and 55–103.
Kempe et al. Gene vol. 39 pp. 239–245 (1985).
Bullesbach et al. Biochem. vol. 25 pp. 5998–6004 (1986).
Lehninger, *Biochemistry*, "The Molecular Basis of Cell Structure and Function", 1975, pp. 202–206.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:1:

```
Ala Phe Ser Lys Ala Phe Ser Lys Ala Phe Ser Lys Ala Phe Ser Lys
 1               5                  10                  15
Ala Phe Ser Lys
            20
```

( 2 ) INFORMATION FOR SEQ ID NO:2:

( i ) SEQUENCE CHARACTERISTICS:

(A) LENGTH: 5 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

Asp Asp Asp Asp Lys
1               5

(2) INFORMATION FOR SEQ ID NO:3:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

Ile Glu Gly Arg
1

(2) INFORMATION FOR SEQ ID NO:4:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:4:

Arg Gly Pro Arg
1

(2) INFORMATION FOR SEQ ID NO:5:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:5:

His Pro Phe His Leu Leu Val Tyr
1               5

(2) INFORMATION FOR SEQ ID NO:6:

(i) SEQUENCE CHARACTERISTICS:
    (A) LENGTH: 30 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:6:

Phe Val Asp Asp Asp Asp Lys Phe Val Asn Gly Pro Arg Ala Met Phe
1               5                   10                  15
Val Asp Asp Asp Asp Lys Val Asn Gly Pro Arg Ala Met Ala
                20                  25                  30

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ile  Asn  Leu  Lys  Ala  Leu  Ala  Ala  Ala  Leu  Ala  Lys  Lys  Ile  Leu
1                  5                            10                           15
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Val  Asp  Asp  Asp  Lys
1                   5
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Lys  Arg  Arg  Trp  Lys  Lys  Asn  Phe  Ala  Val
1                   5                        10
```

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Asn  Gly  Phe  Ser  Pro  Phe  Arg  Gly  Phe  Ser  Pro  Phe  Arg  Gly  Phe  Ser
1                   5                            10                           15
Pro  Phe  Arg
```

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Asn  Gly  Pro  Arg
1
```

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GACGACGACG ATAAA         15

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

ATTGAAGGAA GA         12

( 2 ) INFORMATION FOR SEQ ID NO:14:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

AGAGGACCAA GA         12

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CATCCTTTTC ATCTGCTGGT TTAT         24

CHEMICAL METHOD FOR SELECTIVE MODIFICATION OF THE N- AND/OR C-TERMINAL AMINO ACID α-CARBON REACTIVE GROUP OF A RECOMBINANT POLYPEPTIDE OR A PORTION THEREOF

This is a continuation of application Ser. No. 07/912,798, filed Jul. 13, 1992, abandoned.

BACKGROUND OF THE INVENTION

Many naturally occurring proteins and peptides have been produced by recombinant DNA techniques. Recombinant DNA techniques have made possible the selection, amplification and manipulation of expression of the proteins and peptides. For example, changes in the sequence of the recombinantly produced proteins or peptides can be accomplished by altering the DNA sequence by techniques like site-directed or deletion mutagenesis.

However, some modifications to a recombinantly produced protein or peptide can not be accomplished by altering the DNA sequence. For example, the C-terminal α-carboxyl group in many naturally occurring protein and peptides often exists as an amide, but this amide typically is not produced through recombinant expressing and is biologically converted after expression in vivo from a precursor protein to the amide. Another example is the addition of a D-amino acid to the N- and/or C-terminal end of a recombinantly produced protein or peptide.

In addition, it may be desirable to selectively modify both the N- and C-terminal α-carbon reactive groups of a recombinantly produced protein or peptide. Recombinantly produced protein or polypeptides have a multiplicity of reactive side chain groups, as well as the N- and C-terminal amino acid α-carbon reactive groups. Side chain reactive groups include thiols, carboxyls, imidazoles, and α-amine reactive groups. Selective modifications at the N- and/or C-terminal α-carbon reactive groups, such as adding an N-terminal pyroglutamyl residue and/or forming an amide at the C-terminal amino acid, need to be conducted without adversely affecting the reactive side chain groups.

A method of forming a C-terminal amide on a recombinantly produced polypeptide by the action of an enzyme is known. The enzyme is peptidyl glycine α-amidating monooxygenase and is present in eukaryotic systems. The enzyme has been used to form an amide on the C-terminal amino acid of recombinantly produced peptides, like human growth hormone releasing hormone in vitro as described by J. Engels, *Protein Engineering*, 1:195–199 (1987).

In addition many recombinantly produced small proteins and peptides have a limited number of reactive side chain groups. For example, the 27 amino acid human gastrin releasing peptide contains N-terminal α-amine and side chain hydroxyl and ε-amine reactive groups. The myosin light chain kinase inhibitor contains 10 amino acids and has N-terminal α-amine and side chain ε-amine reactive groups. The C-terminal α-carboxyl groups are amidated in both of these naturally occurring peptides. Although these types of small proteins and peptides have a limited number of different reactive groups, they have been amidated through the traditional method of enzymatic C-terminal amidation. While selective, the enzymatic method is time consuming, expensive, gives unpredictable yields, and requires significant post reaction purification. The enzymatic method is also limited to modifying the recombinantly produced peptide by C-terminal amidation.

Accordingly, there is a need for a chemical method that provides for selective modification of either or both N-terminal α-amine and C-terminal α-carboxyl groups of a recombinantly produced polypeptide. This method results in selective modifications to one or both terminal amino acid α-carbon reactive groups and does not adversely affect the reactive side chain groups. There is also a need for a method of selective modification that allows addition of a variety of different organic moieties to the N- and/or C-terminal α-carbon reactive groups of a recombinantly produced polypeptide and that is convenient, cheap and capable of producing terminally modified recombinant polypeptides in high yield. Therefore, it is an object of the invention to develop a chemical method for selective modification of N-terminal a-amine and/or C-terminal α-carboxyl reactive groups of a recombinantly produced polypeptide.

SUMMARY OF THE INVENTION

These and other objects are accomplished by the present invention. The invention provides for a chemical method for preparing a recombinant single copy polypeptide or portion thereof with a modified terminal amino acid α-carbon reactive group selected from the group consisting of an N-terminal α-amine, C-terminal α-carboxyl and a combination thereof. The recombinant single copy polypeptide also has reactive side chain groups selected from the group consisting of an ε-amine group, a hydroxyl group, a β-carboxyl group, a γ-carboxyl, a thiol group, and a combination thereof.

The steps of the method involve forming the recombinant single copy polypeptide or a portion thereof so that the single copy polypeptide is protected with one or more biologically added protecting groups at the N-terminal α-amine and/or the C-terminal α-carboxyl. The recombinant single copy polypeptide is then reacted with up to three chemical protecting agents to selectively protect reactive side chain groups to form a side chain protected recombinant single copy polypeptide and thereby prevent the side chain group from being modified during the modification reaction. The recombinant single copy polypeptide is cleaved with at least one cleavage reagent specific for the biologically added protecting group to form a recombinant polypeptide with unprotected terminal amino acid α-carbon reactive group. Alternatively, the single copy polypeptide can be cleaved with at least one cleavage reagent specific for the biological protecting group followed by reaction with up to three chemical protecting agents. In either case, a side chain protected single copy polypeptide having an unprotected terminal amino acid α-carbon reactive group is produced. The unprotected terminal amino acid α-carbon reactive group is then modified with at least one chemical modifying agent. The resulting side chain protected terminally modified single copy polypeptide is then deprotected at the side chain groups to form a terminally modified recombinant single copy polypeptide.

The recombinant single copy polypeptide or portion thereof is formed with one or more biologically added protecting group on the terminal amino acid α-carbon reactive groups. The biologically added protecting group can be a peptide, a polypeptide, amino acid, or a combination thereof connected to the N- and/or C-terminal α-carbon reactive groups by an amide bond connection. The biological protecting group bond is stable and generally irreversible and, thus, contains at least one recognition sequence that is cleavable enzymatically or chemically. The recombinant polypeptide with one or more biologically added protecting groups is formed by incorporating the DNA sequence for the biologically added protecting group or groups into the expression cassettes adjacent to the sequence for the recombinantly produced protein or peptide.

For example, the recombinant single copy polypeptide can be formed as a single copy fusion protein. The single copy fusion protein has a binding protein connected via an interconnecting peptide to the single copy polypeptide at either the N- and/or C-terminal α-carbon reactive group. The interconnecting peptide has at least one site that is cleavable by a chemical or enzymatic reagent and serves as a biological protecting group. The binding protein and interconnecting peptide not only serve as a biological protecting group, but also aid in purification of the recombinant single copy polypeptide.

The recombinant single copy polypeptide can also be formed having only a portion of the amino acid sequence of the desired polypeptide or as a truncated version of the polypeptide. Preferably, the portion of the sequence is lacking from about 1 to about 10 of the terminal amino acids of the polypeptide. The portion of the recombinant single copy polypeptide is formed so that it is biologically protected at the N- and/or C-terminal end with a polypeptide, peptide, or amino acid as described above. The portion of or truncated version of the single copy polypeptide can also be formed as a multicopy polypeptide or fusion protein.

The starting material of the invention can also be recombinantly formed as a multicopy polypeptide or fusion protein. The multicopy polypeptide has several copies of the single copy polypeptide tandomly linked together with or without an intraconnecting peptide. If an intraconnecting peptide is present, it has at least one site that is selectively cleavable by a chemical or enzymatic cleavage reagent. The intraconnecting peptide also acts as a biological protecting group at the C-terminal portion of one or more single copy polypeptides incorporated into the multicopy polypeptide. A multicopy fusion protein has three tandomly linked segments including a binding protein connected via an interconnecting peptide to the multicopy polypeptide. The interconnecting peptide has at least one site that is selectively cleavable by a chemical or enzymatic method and is preferably different from the intraconnecting peptide. The binding protein with interconnecting peptide acts as a biological protecting group and aids in the purification of the recombination multicopy polypeptide.

The starting materials of the invention are selected and recombinantly produced with biologically added protecting groups. The starting materials can include a biologically protected recombinant single copy polypeptide or portion thereof, a recombinant single copy fusion protein, a recombinant multicopy fusion protein, and a biologically protected recombinant multicopy polypeptide. The preferred starting material is a recombinant single or multicopy fusion protein.

Once the starting material of the invention is selected and formed, the starting material is treated to produce a protected single copy polypeptide having an unprotected terminal amino acid α-carbon reactive group. The starting material is reacted with up to three chemical protecting agents to form a side chain protected molecule to prevent reaction of side chain reactive groups with the modification agent. The starting material is cleaved with a cleavage reagent specific for the biologically added protecting group to form an unprotected terminal amino acid α-carbon reactive group. The number and sequence of steps of cleaving and reacting the starting material with up to three chemical protecting agents can vary depending on several factors, including:

(a) if the starting material of the invention is a multicopy polypeptide or fusion protein, extra cleavage steps can be required;

(b) if the modification desired is at the N- and/or C-terminal α-carbon reactive group, extra cleavage and modification steps are required;

(c) the amino acid sequence of the desired polypeptide, the number of side chain reactive groups, and whether a cleavage recognition sequence is present will influence whether the polypeptide is protected first or cleaved first; and (d) the type of modification—for example, some types of modification reactions do not require protection of side chain reactive groups.

The number and sequence of cleaving and reacting steps are selected to achieve a protected single copy polypeptide having an unprotected terminal α-carbon reactive group. For example, a recombinant multicopy fusion protein can be terminally modified as follows. The recombinant multicopy fusion protein is recombinantly formed having a binding protein connected to an interconnecting peptide which is connected to the N- or C-terminal end of the multicopy polypeptide. The multicopy polypeptide has several copies of the single copy polypeptide connected with intraconnecting peptides. The interconnecting peptide and intraconnecting peptide act as biological protecting groups and each have at least one chemical or enzymatic cleavage site. The multicopy fusion protein is first cleaved with cleavage reagents specific for the interconnecting peptide to form a multicopy polypeptide. The multicopy polypeptide is then reacted with up to three chemical protecting agent to protect reactive side chain groups followed by cleavage with at least one cleavage reagent specific for the biologically added protecting group or in the reverse order. The cleavage reagent specific for the biologically added protecting groups act to cleave at the intraconnecting peptide and to remove remaining intraconnecting peptide residues. In either case, a protected single copy polypeptide having an unprotected terminal amino acid α-carbon reactive group is produced. The terminal α-carbon reactive group is modified. The terminally modified single copy polypeptide is deprotected to yield a terminally modified recombinant single copy polypeptide.

The unprotected terminal α-carbon reactive groups can be modified by reaction with a chemical modifying agent. The modifying agent acts to add or replace terminal amino acids with organic moieties. Specific examples of types of modifications include: C-terminal amidation; addition or replacement of terminal amino acids with a D-amino acid, an L-amino acid, an amino acid derivative, or peptides having a combination thereof; or formation of an N-acetyl group. Modification can occur at one or both terminal α-carbon reactive groups.

Once a protected recombinant single copy polypeptide is modified, it is deprotected under conditions allowing regeneration of the original side chain reactive groups. The final product is a terminally modified recombinantly produced single copy polypeptide. Modifications can change the biological activity or structure of the desired recombinant polypeptide.

DETAILED DESCRIPTION OF THE INVENTION

Recombinant DNA techniques have made possible the selection, amplification, and manipulation of expression of many naturally occurring proteins and peptides. Naturally occurring proteins and peptides recombinantly produced generally contain a multiplicity of amino acids having side chains with different functional or reactive groups including hydroxyl, thiols, carboxyls, and ε-amine groups. Two other important reactive groups are the N-terminal α-amine reactive group and the C-terminal α-carboxyl reactive group. It is often desirable to selectively modify a recombinant polypeptide at the N-terminal α-amine and/or C-terminal α-carboxyl groups. For example, the C-terminal reactive carboxyl groups in some naturally occurring proteins and peptides can be selectively converted to an amide to provide for enhancement of biological activity. Alternatively, a D-amino acid or peptide could be added to or replace a terminal amino acid.

These modifications can result in the formation of analogs of the recombinantly produced polypeptide that are longer acting and more potent than the naturally occurring polypeptide. Generally, these types of modifications to the recombinantly produced polypeptide are not accomplished by alteration of the DNA sequence for the recombinantly produced polypeptide because there is no genetic code providing for amino acid amides, or incorporation of D-amino acid or an amino acid derivative.

The present invention provides a method for the selective modification of a recombinantly produced polypeptide at a terminal α-carbon reactive group selected from the group consisting of N-terminal α-amine, C-terminal α-carboxyl and a combination thereof. The first step in the method is to form the recombinantly produced single or multicopy polypeptide so that it is protected at one or both terminal α-carbon reactive groups with a biologically added protecting group.

The biologically added protecting group is preferably an amino acid, peptide, and/or polypeptide that contains at least one site that is cleavable enzymatically or chemically, and preferably has a sequence that is not present in the sequence of the desired polypeptide. The biologically added protecting group can be added to the recombinantly produced polypeptide by combining the DNA sequence for the biologically added protecting group to the 5' and/or 3' terminus of the gene encoding the desired polypeptide. Once formed, the recombinantly produced polypeptide, biologically protected at the terminal α-carbon reactive groups, is reacted with up to three chemical protecting agents to protect the side chain groups and then is cleaved with at least one cleavage reagent specific for at least one biologically added protecting group. Alternatively, the recombinant single copy polypeptide, biologically protected at the terminal α-carbon reactive group, is cleaved with a cleavage reagent specific for at least one biologically added protecting group and then reacted with up to three chemical protecting agents that act to protect side chain reactive groups. In either case, a polypeptide is produced having an unprotected N- or C-terminal α-carbon reactive group and protected side chain reactive groups. The unprotected terminal amino acid α-carbon reactive group is modified with a modifying agent to form a terminally modified protected single copy polypeptide. The terminally protected single copy polypeptide is then deprotected to form an N- and/or C-terminally modified single copy polypeptide.

The sequence and number of steps in the method of the invention can be varied depending on the desired modification, the amino acid sequence of the desired polypeptide, and the starting material selected. The starting materials of the invention can include a recombinantly produced single copy polypeptide, or a portion thereof, a multicopy polypeptide, a single copy fusion protein, and a multicopy fusion protein.

For example, the method of the invention provides for the selective N-terminal α-amine and C-terminal α-carboxyl modification of a recombinantly produced single copy polypeptide. A recombinantly produced single copy polypeptide is formed so that the N-terminal α-amine is biologically protected by an amide bond connection to an interconnecting peptide and a binding protein and the C-terminal α-carboxyl is biologically protected by an amide bond connection to an arginine residue. The recombinant single copy polypeptide biologically protected at both the N- and C-terminal α-carbon reactive groups is then reacted with up to three chemical protecting agents so that the reactive side chain groups present in the recombinant single copy polypeptide are protected and not available to react with the modifying agent. The protected single copy polypeptide is then cleaved with a cleavage reagent specific for the N-terminal biological protecting group and the unprotected α-amine group is reacted with a chemical modifying reagent. The modified side chain protected single copy polypeptide is then cleaved with a cleavage reagent specific for the C-terminal biological protecting group. The unprotected C-terminal α-carboxyl group is reacted with a second modifying agent to form a side chain protected N-terminal modified, C-terminal modified single copy polypeptide. The protected N-terminal, C-terminal modified single copy polypeptide is deprotected at the side chain reactive groups to form a recombinant single copy polypeptide modified at the N- and C-terminal ends of the molecule. The reaction scheme showing sequential N-terminal α-amine and C-terminal α-carboxyl modification of a recombinant single copy polypeptide is as follows:

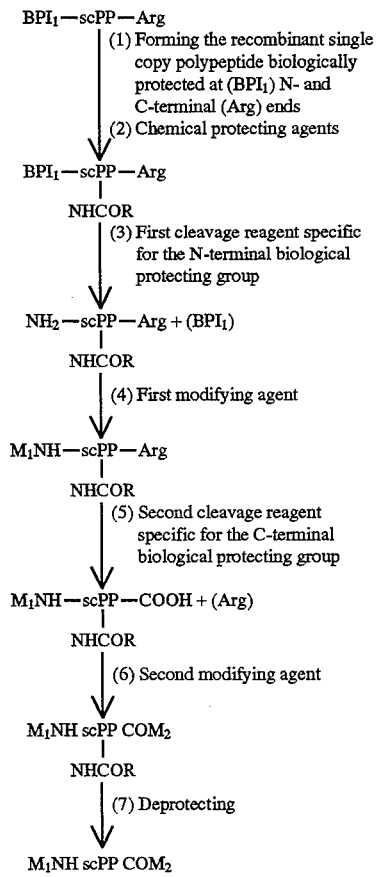

Reaction Scheme I:
Selective Modification at the N- and C-Terminal Amino Acid of a Recombinant Single Copy Polypeptide $BPI_1$—scPP—Arg (1) Forming the recombinant single copy polypeptide biologically protected at ($BPI_1$) N- and C-terminal (Arg) ends
(2) Chemical protecting agents $BPI_1$—scPP—Arg
 |
 NHCOR (3) First cleavage reagent specific for the N-terminal biological protecting group $NH_2$—scPP—Arg + ($BPI_1$)
 |
 NHCOR (4) First modifying agent $M_1NH$—scPP—Arg
 |
 NHCOR (5) Second cleavage reagent specific for the C-terminal biological protecting group $M_1NH$—scPP—COOH + (Arg)
 |
 NHCOR (6) Second modifying agent $M_1NH$ scPP $COM_2$
 |
 NHCOR (7) Deprotecting $M_1NH$ scPP $COM_2$

Reaction Scheme I:
Selective Modification at the N- and C-Terminal Amino Acid of a Recombinant Single Copy Polypeptide Key $BPI_1$—scPP—Arg = recombinant single copy fusion protein (scPP) biologically protected a N-terminal α-amine by an amide bond to a binding protein (BP) and interconnecting peptide ($I_1$) and protedted at the C-terminal α-carboxyl with an arginine (Arg) residue $BPI_1$—scPP—Arg
    |
 NHCOR
= recombinant single copy polypeptide protected at the side chain reactive groups (NHCOR)

$NH_2$—scPP—Arg
    |
 NHCOR
= side chain protected recombinant single copy polypeptide with unprotected N-terminal α-amine ($NH_2$)

$M_1NH$—scPP—Arg
    |
 NHCOR
= side chain protected recombinant single copy polypeptide with modified N-terminal α-amine ($NHM_1$)

$M_1NH$—scPP—COOH
    |
 NHCOR
= N-terminally modified side chain protected recombinant single copy polypeptide with unprotected C-terminal α-carboxyl group $M_1NH$—scPP—$COM_2$
    |
 NHCOR
= C-terminal ($COM_2$) modified side chain protected single copy polypeptide $M_1NH$—scPP—$COM_2$ = N and C terminally modified single copy polypeptide Another variation of the method of the invention involves C-terminal modification of a single copy polypeptide derived from a recombinantly produced multicopy polypeptide. The multicopy polypeptide is formed with multiple copies of the desired polypeptide connected with intraconnecting peptides. The intraconnecting peptide acts as a biological protecting group for the C-terminal α-carboxyl reactive group of the single copy polypeptides. The recombinantly produced multicopy polypeptide is cleaved with a cleavage reagent specific for the intraconnecting peptide to form a first mixture of a single copy polypeptide with unprotected N-terminal α-amine and an unprotected C-terminal α-carboxyl group and a single copy polypeptide with an unprotected N-terminal α-amine and an intraconnecting peptide at the C-terminal α-carboxyl group. The first mixture is reacted with at least one chemical protecting agent that forms protecting groups at the reactive side chain groups and the unprotected N-terminal α-amine reactive group. The intraconnecting peptide at the C-terminal α-carboxyl group is then removed by cleavage with a cleavage reagent that digests the intraconnecting peptide residues to form a side chain protected single copy polypeptide having an unprotected C-terminal α-carboxyl group. The unprotected C-terminal α-carboxyl group is then modified with a modifying agent. The side chain protected single copy polypeptide with modified C-terminal α-carboxyl group is then deprotected to form the C-terminal modified single copy polypeptide. The reaction scheme depicting selective C-terminal modification of single copy polypeptide derived from a recombinantly produced multicopy polypeptide is as follows:

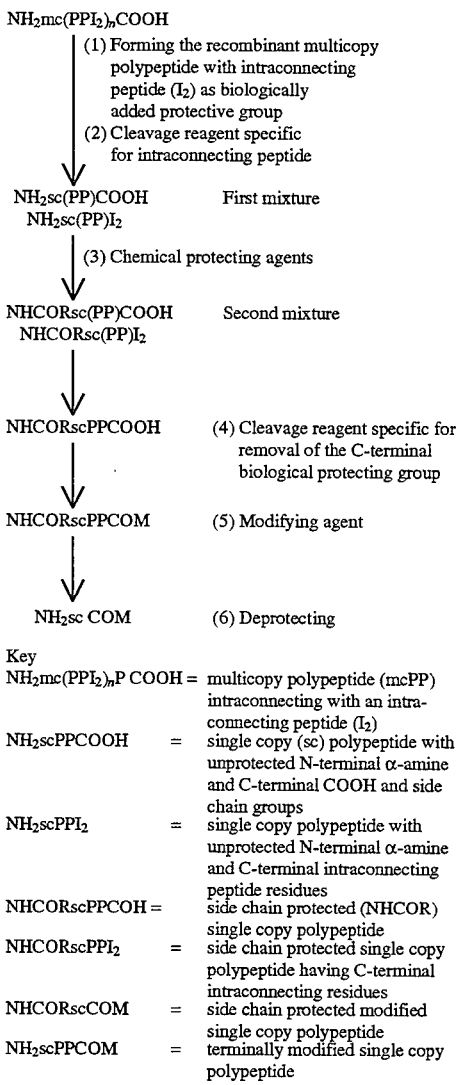

Reaction Scheme II:
Selective C-terminal Modification of a Single Copy Polypeptide Derived from a Recombinant Multicopy Polypeptide Other variations of the method of the invention involving the number and sequence of the steps can be utilized to achieve selective modification of the N- and/or C-terminal α-carbon reactive group of a recombinantly produced polypeptide. The combination of steps that will be appropriate to result in selective N- and/or C-terminal modification depends on the selection of:

(a) the starting material—a multicopy polypeptide or fusion protein can require additional cleavage steps to form single copy polypeptides;

(b) whether the modification is at the N- and/or C-terminal α-carbon reactive group, N- and C-terminal modification requires extra steps;

(c) the amino acid sequence of the desired polypeptide, especially the number of different side chain reactive groups and whether a cleavage recognition sequence is present in the sequence of the polypeptide; and (d) the type of modification, some types of modification do not require protection of the side chain groups.

A. Preparation of the Starting Materials: Forming the Recombinant Polypeptide Biologically Protected at the N- and/or C-Terminal α-Carbon Reactive Group

1. Selecting the Desired Peptide and the Modification

A polypeptide is a polymer of amino acids linked by amide bonds having a terminal amino acid with a reactive α-amine group at one end (N-terminal) and a terminal amino acid with a reactive α-carboxyl group at the other end (C-terminal). A polypeptide typically has at least one reactive or functional amine group including the N-terminal α-amine group. In addition, the polypeptide can have one or more reactive side chains including ε-amino groups of lysine. Other amino acids have side chains with reactive or functional groups like thiol, hydroxyl, phenolic hydroxyl, imidazole and carboxylic acid groups. A recombinantly produced polypeptide is a polypeptide that is produced by isolating or synthesizing the gene for the polypeptide and introducing the gene into a vector which allows for the amplification and manipulation of expression of the gene in a host organism.

The starting material is selected, designed and then recombinantly produced. The starting material is selected according to such factors as:

(a) the characteristics of the desired polypeptide including the desired modification, size and amino acid composition;

(b) whether the modification is to be made at the N- and/or C-terminal amino acid α-carbon reactive group requiring biologically added protecting groups at one or both ends of the molecule; and (c) ease of purification, to enhance purification of the recombinantly produced polypeptide a single or multicopy fusion protein can be formed.

Before the starting material of the invention is formed, the desired polypeptide is selected because of its function, size, and amino acid composition.

The function of the polypeptide selected for the method of the invention can be altered by selective modification of the N- and/or C-terminal amino acid. Modifications to the polypeptide can change the structural characteristics and/or the biological activity of the polypeptide. For example, C-terminal amidation of many small peptides, like mastoparan or the human gastrin releasing peptide, enhances the biological activity of these peptides. Moreover, addition of peptides having D- or L-amino acids can provide for targeting of the polypeptide to a specific cell type, changing the rate of breakdown and clearance of the peptide, increasing the biological potency and increasing the biological activities of the polypeptide. Addition of D-amino acids or peptides or derivatives of amino acids can also result in the formation of antagonists. The choice of polypeptide and modification can be made based upon the desired change of the structural or biological activity of the peptide. The especially preferred modification is C-terminal amidation of a peptide.

Several examples of modified polypeptides and the changes in biological activity associated with this modification are described in *Kirk-Othmer Encyclopedia of Chemical Technology*, 4th Edition, Vol. 12, pp. 603–617 (1991), which is hereby incorporated by reference.

The size of the selected polypeptide can range from a peptide of about 4 amino acids to a polypeptide of about 4000 amino acids (about 500,000 daltons). The larger polypeptides are typically recombinantly produced as a single copy fusion protein or polypeptide. Smaller peptides having 50 amino acids or less are preferably produced as multicopy fusion proteins or polypeptides. Especially preferred are small biologically active peptides having 50 amino acids or less.

The amino acid composition of the desired polypeptide can have a multiplicity of side chain functional reactive groups, but the method is preferably directed to polypeptides having one or two types of reactive side chain groups. For example, especially preferred polypeptides are those having only ε-amine groups as reactive side chain groups. Other especially preferred polypeptides are those having ε-amino and hydroxyl or carboxyl side chain groups. Many small biologically active peptides, like the magainin polypeptides, have limited types of functional or reactive side chain groups.

Specific examples of polypeptides having one or two types of reactive side chain groups include the magainin polypeptides I, II and III, as disclosed by Zasloff et al. in U.S. Pat. No. 4,810,777 (issued Mar. 7, 1989); and wound healing peptide like Ala-Phe-Ser-Lys-Ala-Phe-Ser-Lys-Ala-Phe-Ser-Lys-Ala-Phe-Ser-Lys-Ala-Phe-Ser-Lys (SEQ ID NO:1), as disclosed by Berkowitz et al. in U.S. Pat. No. 5,045,531 (issued Sep. 3, 1991). These disclosures are hereby incorporated by reference.

Other examples of suitable polypeptides include the myosin light chain kinase inhibitor, substance P, mastoparan, mastoparan X, human amylin, rat amylin, Icaria chemotactic peptide, carassin, human gastrin releasing peptide, kemptamide, myosin kinase inhibiting peptide, melettin, [Leu$^5$]-enkephalamide, [Met$^5$]-enkephalamide, metrophenamide, ScP$_B$, allatostatin 1, allatostatin 3, crustacean cardioactive peptide, FMRF (molluscan cardioexcitatory neuropeptide), FMRF-like peptide F1, neuromedian B, bombesin, leukopyrokinin, alyetesin, corazonin and littorin.

Once the desired polypeptide and modification is selected, the starting material can be designed and recombinantly produced so that the N- and/or C-terminal α-carbon reactive group has a biologically added protecting group.

2. Selecting The Biologically Added Protecting Groups To Be Added to the N- and/or C-Terminal α-Carbon Reactive Group of the Polypeptide Before the starting material is formed, the biologically added protecting groups are selected. The biologically added protecting groups can be a polypeptide, peptide and/or amino acid linked by an amide bond connection to the N- and/or C-terminal α-carbon reactive group. The type of bond formed is generally irreversible and the sequence of the biological protecting group contains at least one site that is cleavable enzymatically or chemically so that the biological protecting group can be selectively removed. Preferably, the sequence of the biologically added protecting group is not present in the desired polypeptide. When both the N- and C-terminal α-carbon reactive groups are protected with the biologically added protecting groups, the biologically added protecting group at the N-terminal α-carbon reactive group is preferably different from the group at the C-terminal α-carbon reactive group to allow for sequential cleavage of the N- and C-terminal biologically added protecting group.

The biologically added protecting group has at least one cleavage site to provide for removal of all or part of the biological protecting group. Specific examples of peptides and amino acids that can serve as a cleavage site in biological protecting groups and the cleavage enzymes or conditions are provided in Table 1.

TABLE 1

| Enzymes for Cleavage | Biological Protecting Groups | DNA Seq. |
|---|---|---|
| Enterokinase | (Asp)$_4$Lys (SEQ ID NO: 2) | GACGACGACGATAAA (SEQ ID NO: 12) |
| Factor Xa | IleGluGlyArg (SEQ ID NO: 3) | ATTGAAGGAAGA (SEQ ID NO: 13) |
| Thrombin | ArgGlyProArg (SEQ ID NO: 4) | AGAGGACCAAGA (SEQ ID NO: 14) |
| Ubiquitin Cleaving Enzyme | ArgGlyGly | AGAGGAGGA |
| Renin | HisProPheHisLeu-LeuValTyr (SEQ ID NO: 5) | CATCCTTTTCATC-TGCTGGTTTAT (SEQ ID NO: 15) |
| Trypsin | Lys or Arg | AAA OR CGT |
| Chymotrypsin | Phe or Tyr or Trp | TTT or TAT or TGG |
| Clostripain | Arg | CGT |
| S. aureus V8 | Glu | GAA |
| Chemical Cleavage | Biological Protecting Groups | DNA Seq. |
| (at pH3) | AspGly or AspPro | GATGGA |
| (Hydroxylamine) | AsnGly | AATCCA |
| (CNBr) | Methionine | ATG |
| BNPS-skatole | Trp | TGG |
| 2-Nitro-5-thiocyanobenzoate | Cys | TGT |

The biological protecting group can contain more than one enzymatic and/or chemical cleavage site, and preferably contains at least one site cleaved by a chemical reagent and at least one site cleaved by an enzyme. Alternatively, the biological protecting group can have at least two different enzymatic sites of cleavage or at least two different chemical cleavage sites. A specific example of a biological protecting group having multiple cleavage sites is exemplified by the following peptide:

Phe Val Asp Asp Asp Asp Lys$_A$ Phe Val Asn$_B$ Gly Pro Arg$_C$ Ala Met$_D$ Phe Val Asp Asp Asp Asp Lys$_A$ Val Asn$_B$ Gly Pro Arg$_C$ Ala Met$_D$ Ala (SEQ ID NO:6)

A=cleavage site for enterokinase
B=cleavage site for hydroxylamine
C=cleavage site for thrombin
D=cleavage site for cyanogen bromide The biological protecting group with multiple cleavage sites can also serve as an interconnecting or intraconnecting peptide. While not in any way meant to limit the invention, the combination of chemical and enzymatic cleavage sequence in biologically protected group provides for advantages in purification and cleavage efficiency.

The biological protecting group can also be a combination of a polypeptide and a peptide like, for example, in a recombinant single copy fusion protein. A recombinant single copy fusion protein has three tandomly coupled segments. The first segment is a binding protein, the second segment is an interconnecting peptide, and the third segment is the single copy polypeptide. The interconnecting peptide connects the binding protein to the single copy polypeptide at either the N- or C-terminal α-carbon reactive group. The interconnecting peptide has at least one chemical or enzymatic cleavage site and, preferably, has a sequence not found in the single copy polypeptide. The binding protein and interconnecting peptide serve as the biologically added protecting group at the N-terminal α-amine or C-terminal α-carboxyl group and also provide for purification of the recombinantly derived single copy polypeptide.

Another example is recombinant multicopy fusion protein composed of three tandomly coupled segments. The first segment is a binding protein, the second segment is an interconnecting peptide, and the third segment is a multicopy polypeptide. The interconnecting peptide connects the binding protein to the N- or C-terminal α-carbon reactive group of the multicopy polypeptide. The multicopy polypeptide contains several copies of the single copy polypeptide connected by an intraconnecting peptide. The inter- and intraconnecting peptides both have at least one site that is cleavable and preferably do not contain amino acid sequence present in the single copy polypeptide. The interconnecting peptide and the intraconnecting peptide can act as biological protecting groups of the N- and/or C-terminal α-carbon reactive groups of the single or multicopy polypeptide. When both the C-terminal and N-terminal α-carbon reactive groups are to be modified, preferably the inter- and intraconnecting peptide have different cleavage sites to provide for sequential cleavage.

Once the polypeptide and the desired modification are selected, the protecting groups to be biologically added to the N- and/or C-terminal α-carbon reactive groups are selected. The factors for selecting the biologically added protecting groups to be combined with the desired polypeptide include: (a) the amino acid sequence of the single copy polypeptide; (b) whether the polypeptide is going to be recombinantly produced as a single or multicopy polypeptide; (c) whether a single or multiple cleavage site is desired; (d) whether enzymatic or chemical cleavage is desired; (e) whether a fusion protein is desired to provide for purification; and (f) compatibility of the amino acid sequence of the biological protecting group with the chemical protecting agents.

3. Forming the Recombinant Single or Multicopy Polypeptide Protected with One or More Biologically Added Protecting Groups at the N- and/or C-Terminal α-Carbon Reactive Groups By Standard Recombinant DNA Methodology The single or multicopy polypeptide or fusion protein starting material of the method of the invention is formed by standard recombinant DNA methods. The gene sequence for the desired polypeptide or a portion thereof can be cloned or, in the case of a smaller peptide, synthesized by automated synthesis. The gene sequence encoding the biologically added protecting group is synthesized by automated oligonucleotide synthesis. The gene sequence for the biologically added protecting group is combined with the gene sequence for a single or multicopy polypeptide or a portion thereof so that the single or multicopy polypeptide produced has at least one cleavable biologically added protecting group at the N- and/or C-terminal α-carbon reactive group.

The gene sequence for the biologically added protecting group encodes a polypeptide, peptide, amino acid, or a combination thereof. Preferably, the gene sequence encodes a peptide of less than about 50 amino acids and provides for one site of cleavage by a chemical reagent and at least one site of enzymatic cleavage. Once the biological protecting group is selected, the DNA sequence is formed by automated synthesis and combined with the gene sequence for the single or multicopy polypeptide by standard recombinant DNA methodologies. Specific examples of the DNA sequences that correspond to amino acid cleavage sites are provided in Table 1. The DNA sequences encoding chemical and enzymatic cleavage sites can be combined into a gene sequence for a single biological protecting group by automated oligonucleotide synthesis.

The single or multicopy polypeptide can also be formed as a recombinant single or multicopy fusion protein. The fusion protein has three tandomly coupled segments. The first segment is a binding protein, which exhibits strong, reversible binding. The second segment is an interconnecting peptide, which is selectively cleavable by an enzyme and/or chemical technique. The third segment is the single or multicopy polypeptide. The binding protein with interconnecting peptide provides for purification of the recombinantly produced single or multicopy polypeptide and acts as a biological protecting group for the N- or C-terminal α-carbon reactive group. Single or multicopy fusion proteins are produced by standard recombinant DNA methodology, as discussed in co-pending application Ser. No. 07/552,810, which is hereby incorporated by reference. Formation of recombinantly produced single or multicopy fusion proteins is described.

The binding protein segment of the fusion protein generally is an antibody, an antibody L or H chain, an enzyme, a lectin, avidin or any expression protein having a binding site for selective binding to a ligand such as an antigen, a substrate, an inhibitor, a sugar or biotin. Preferably, the binding protein is an enzyme-like protein including but not limited to an enzyme or a truncated, altered or modified functional version thereof (hereinafter the modified functional version). The binding is preferably strong and selective. Preferably for an enzyme the ligand is a reversible inhibitor for the enzyme-like protein.

Especially preferred embodiments of the enzyme binding protein include carbonic anhydrase derived from any source, especially mammalian or human, and a modified functional version thereof which will bind with the inhibitor, sulfanilamide or derivatives thereof. An especially preferred embodiment of the modified carbonic anhydrase enzyme is a functional version which (I) does not contain methionine, (II) has all or some glutamates replaced by another amino acid, preferably aspartate, (III) has all or some arginines replaced by another amino acid, preferably lysine, (IV) has asparagines next to glycine replaced by another amino acid, preferably glutamine or glycine changed to alanine, (V) has methionine replaced by another amino acid, preferably leucine, and (VI) has cysteine replaced by another amino acid, preferably serine.

Antibodies or individual chains, regions or fragments thereof, as characterized above, and other proteins, which will strongly, biospecifically and reversibly bind to a low molecular weight ligand, can perform the same function in the same way to reach the same result as the enzyme-like protein in the context of the protein purification construct, and consequently are also preferred within the invention as binding proteins. For antibodies or the corresponding chains, regions or fragments, the ligand is a low molecular weight antigen, preferably an aromatic moiety such as dinitrophenol.

Suitable binding proteins and their corresponding ligands include those provided in Table 2.

TABLE 2

| Binding Protein | Ligand | Kd | Ref. |
|---|---|---|---|
| Xanthine Oxidase | Allopurinol | strong | 1 |
| Adenosine deaminase | Coformycin | <1.2E-10 | 1 |
| Adenosine deaminase | Deoxycoformycin | 2.5E-12 | 2 |
| Adenosine deaminase | erythro-9-(2-hydroxy-3 nonyl) adenine | 1.6E-9 | 2 |
| Dihydrofolate reductase | Methotrexate | 1.2E-9 | 4 |
| Dihydrofolate reductase | Methotrexate | 2.3E-9 | 5 |
| Dihydrofolate reductase | Aminopterin | 3.7E-9 | 5 |
| Dihydrofolate reductase | Trimethoprin | 4.6E-9 | 5 |
| Ribulose bisphosphate carboxylase | 2 carboxyarabirital 1,5 bisphosphate | 1E-16 | 6 |
| Pepsin | Pepstatin | 10E-9 | |
| Calmodulin | Melittin | 3E-9 | 7 |
| Calmodulin | Various peptides | 0.2E-9 | 7 |
| Cholesterol esterase | Borinic acid | 0.1E-9 | 8 |
| Carbonic anhydrase II | Sulfanilamide | 4.6E-7 | 3 |
| Carbonic anhydrase II | Acetazolamide | 6 E-10 | 3 |

E is times ten to the negative exponent indicated.
References Cited in Table 2
1. Cha et al., Biochemical Pharm., 24, 2187–2197.
2. Agarwal et al., Biochemical Pharm., 26, 354–367 (1977).
3. Taylor, P.W. et al., Biochemistry, 9, 2638 (1970).
4. Cha et al., Biochemical Pharm., 30, 1507–1515 (1981).
5. Williams et al., Biochemical Pharm., 29, 589–595 (1980).
6. Pierce, J., Tolbert, N.E., Barker, R., Biochem., 19:934–942 (1980).
7. Degrado et al., J. of Cellular Biochem., 29, 83–93 (1989).
8. Sutton et al., BBRC, 134, 386–392 (1986).

Other suitable binding proteins include β-galactosidase as described by Hanada et al., J. Biol. Chem., 263:7181 (1988); flagellin protein as described by Stahl et al., U.S. Pat. No. 4,801,526 (issued Jan. 31, 1989); ubiquitin, Yoo et al., J. Biol. Chem., 264:17078 (1989); protein A, B. Nillson et al., EMBO Journal, 4:1075 (1985); streptavidin, Meade et al., PCT/US 85/01901 (1986); and the flag peptide, K. Itakura et al., Science., 198:1056 (1977), which are hereby incorporated by reference.

The choice of the interconnecting or intraconnecting peptide for the single or multicopy fusion protein depends upon the choice of cleavage enzyme and product peptide sequence. In general, the interconnecting peptide sequence constitutes any peptide sequence that uniquely reacts with a highly specific cleavage enzyme or by a highly specific chemical reagent cleavage, or combination thereof, like those shown in Table 1. The interconnecting or intraconnecting peptide is connected to the N- and/or C-terminal α-carbon reactive group and also serves as a biologically added protecting group.

Generally, the interconnecting peptide, and the intraconnecting peptide fragments will have different amino acid sequences so that they can be sequentially rather than simultaneously cleaved. The amino acid sequences can be chosen also so that the cleavage sequence does not duplicate any amino acid sequence of the product peptide(s). Alternatively, the cleavage specific amino acids in the peptide can be blocked or protected from the cleavage reaction as provided in the method of the invention. These peptide and/or amino acid connecting fragments can be chosen from the same group of amino acid unit sequences for example, those listed in Table 1. The factors to consider in choosing these peptide connecting fragments are similar to those for selecting other biological protecting groups and include the following:

a) The amino acid sequence of the product peptides;
b) Whether the polypeptide is a single or multicopy polypeptide;
c) Whether a single or multi cleavage site is desired;
d) Whether enzymatic or chemical cleavage is desired;
e) Whether the intra- and interconnecting peptides and the gene fragments coding for them are positioned and altered to provide for diversity in the gene sequence for the variable fused peptide. This diversity allows efficient expression of multiple units of a small peptide. It has been discovered that a continuously repetitive genetic sequence will often be rearranged or deleted by the host organism prior to recombination.

The recombinantly produced single or multicopy polypeptide with N- and/or C-terminal biologically added protecting groups is produced by standard recombinant DNA methods. An expression cassette can be formed by combining the gene for the single or multicopy polypeptide and the gene encoding the desired biological protecting group with transcriptional and translational control regions. For example, the recombinant gene encoding the fusion protein incorporates three DNA segments coding for the binding protein, the interconnecting peptide and the single or multicopy polypeptide. The segments are arranged so that either the binding protein gene fragment or the single or multicopy polypeptide fragment can be read first. It is preferred to construct the fusion protein gene so that the binding protein gene fragment is read first. The gene segments can be synthetic or derived from natural sources. The fusion protein gene is combined with transcriptional and translational control regions to form an expression cassette.

An expression vector containing the expression cassette is capable of providing for expression of the biologically protected single or multicopy polypeptide in prokaryotic or eukaryotic cells. The expression vector incorporates the single or multicopy polypeptide gene and base vector segments such as the appropriate regulatory DNA sequences for transcription, translation, phenotyping, temporal or other control of expression, RNA binding and post-expression manipulation of the expressed product. The expression vector generally will include structural features such as a promoter, an operator, a regulatory sequence and a transcription termination signal. The expression vector can be synthesized from any base vector that is compatible with the host cell or higher organism and will provide the foregoing features. The regulatory sequences of the expression vector will be specifically compatible or adapted in some fashion to be compatible with prokaryotic or eukaryotic host cells or higher organisms. Post-expression regulatory sequences, which cause secretion of the fusion protein can be included in the eukaryotic expression vector. It is especially preferred that the expression vector exhibit a stimulatory effect upon the host cell or higher organism such that the fusion protein is overproduced relative to the usual biosynthetic expression of the host.

In one preferred scheme for construction of the vector, the DNA segment for the binding protein, for example the human gene for carbonic anhydrase II, (the binding protein gene) is inserted into a base plasmid which is compatible with the host cell to be transformed. The base plasmid contains the necessary regulatory sequences for high level expression of genes placed downstream.

A synthetic DNA sequence coding for the interconnecting peptide is then inserted near the 3' end of the binding protein gene. A restriction enzyme site near the 3' end of the binding protein gene should be present to enable insertion of this DNA sequence for the interconnecting peptide. Also, at least one convenient restriction enzyme site (intermediate vector restriction site) should be designed into the synthetic DNA sequence for the interconnecting peptide so that DNA segments coding for the variable fused polypeptide can later be inserted in the correct reading frame. If no such sites are already present, they can be introduced at this point in the scheme by a site-specific mutagenesis after standard procedures described in Sambrook, J., Fritsch, E. F. and Maniatis, T., *Molecular Cloning, A Laboratory Manual,* Cold Spring Harbor Laboratory, Cold Spring Harbor, N.Y. (1989), the disclosure of which is incorporated herein by reference.

The resulting vector construct is the intermediate base vector for the in situ construction of the fusion protein gene integrated into the larger vector. Any naturally occurring or synthetic DNA sequence encoding a single or multicopy polypeptide can be inserted into the intermediate vector restriction site to yield a fusion protein gene integrated into the expression vector. Proper insertion and reading frame alignment can be verified by known techniques such as sequencing the junction region between the binding protein gene and the DNA sequence for the variable fused polypeptide according to methods described in Sambrook et al.

In a second alternative, after ligating together any two adjacent DNA segments, the resulting intermediate gene can be transferred to the base vector by the restriction and ligation methods described above. The third DNA segment (i.e., the binding protein gene or variable fused polypeptide gene) can be inserted into the base vector carrying the intermediate gene pursuant to the Sambrook techniques including construction of appropriate restriction sites, if needed, and ligation procedures described above. All protocols for restriction, insertion, ligation and the like follow standard procedures such as those described by Sambrook, cited supra.

Preferred base vectors include any plasmid that is compatible with the particular host, is stable in that host and allows for a positive selection of the transformed host. Such vectors include, for example, pTZ18/19U/R or pPL-lambda as well as those characterized in P. H. Pouwels, B. E. Enger-Valk, and W. J. Branimer, *Cloning Vectors,* Elsevier Science Pub. (1985) the disclosure of which is incorporated herein by reference.

The final recombinant expression vector will carry an appropriate promoter, a sequence coding for a ribosome binding site, phenotype genes for selection, and regulatory regions for transcription, translation and for post-translational intracellular manipulation of the resulting biologically protected single or multicopy polypeptide.

The expression vector is introduced into prokaryotic or eukaryotic host cells by standard methods like calcium phosphate precipitation, electroporation and microinjection. Isolation of host cells transformed with the final recombinant expression vector is accomplished by selecting for the phenotype or other characteristic that is designed into the recombinant vector. Generally, such selection characteristics include antibiotic resistance or complementation of deficient functions in the host. Preferred phenotype genes for the recombinant vector of the invention include antibiotic resistent phenotypes, essential amino acid phenotypes and other essential compound phenotypes.

Preferably, an inducible expression system is used so that the selected, transformed host cell will be grown to an early- to mid-logarithmic phase and treated with an induction compound to cause the biologically protected single or multicopy polypeptide to be produced. Typically, incubation will be continued for up to several hours (the most appropriate incubation time for each single or multicopy polypeptide is determined by sampling at differing times during a test incubation), at which point the cells are harvested and lysed. If the transformed host cell is designed to secrete the biologically protected single or multicopy polypeptide, the culture is grown until an appropriate and/or desired concentration of the polypeptide is present in the culture medium. If the host cell is one that will contain dissolved polypeptide in its cytoplasm, the culture is grown until it reaches optimum maturity. The mature culture is then lysed with an appropriate agent to release the polypeptide. If the polypeptide or fusion protein is deposited as insoluble granules in the host cell, the mature cell culture is lysed and the released insoluble granules are dissolved in chaotropic agents. This incubation, growth and lysing process can be conducted in a batch or continuous manner.

The transformed cells are capable of expressing polypeptides containing multiple copies of the polypeptides up to a molecular weight of the largest protein naturally expressed by the cell. For prokaryotic cells, this means that the size of the recombinant protein expressed usually will be smaller than about 500,000 daltons. This is the size of certain enzymes naturally produced, for example by *E. coli* and *Bacillus subtilis*, as disclosed by B. Lewin, in *Genes*, 4th Edition, pages 606–607, Oxford Press, New York, N.Y. (1990), which is incorporated herein by reference. Although eukaryotic cells utilize proteins of a larger size than about 500,000 daltons, typically those larger proteins are expressed as subunits and assembled by post-expression manipulation in such cells. Examples of such larger proteins include hemoglobin and antibodies. Although not meant in any way to limit the invention, it is believed that the expression of very large proteins (greater than 500,000 daltons) is limited by the translational error frequency which approaches 50% during synthesis of a very large protein.

Other factors, as well, can influence the control and extent of expression of the fusion protein in cells transformed with recombinant expression vector. Optimal expression of a multicopy expression cassette or vector can be achieved if the recombinant expression vector is constructed using these factors.

The first factor is that the gene sequence for the multicopy protein should have variations in the gene sequence. This variation avoids a high degree of repetition along the gene sequence and the protein sequence. Such repetition endangers both the gene and expressed fusion protein because the cell will recognize the repetition sequence and excise or assimilate the sequence or protein.

The second factor is that the binding protein gene segment should have a size like that for an enzyme. The size minimizes or prevents variation of translational efficiency due to the needed variation of the gene segment for the desired protein. The latter gene segment variation is important for the reason mentioned above. If the leader sequence is short, the cell will recognize a variation in the tail sequences as a signal to lower the expression efficiency for the protein.

The third factor is that certain polypeptides present in the multicopy alternative achieve a greater increase in yield efficiency than others. This efficiency depends on the ratio of the weight of the binding protein to the weight of the desired protein. Above a certain number of copies, the yield efficiency does not appreciably increase for total molecular weights greater than 250,000 daltons.

The fourth factor is that the expressed protein should be soluble or form granules (inclusion bodies) in the cytoplasm of the transformed cell. Purification and post-expression manipulation of the fusion protein is more readily accomplished when the fusion protein is soluble or forms granules.

The fifth factor is that a strongly bound inhibitor/enzyme couple is employed to separate and purify the fusion protein. In order to achieve this goal, the fusion protein should maintain essentially the same binding constant between the enzyme and its inhibitor as is exhibited by the free enzyme in the inhibitor.

Although the formation of a recombinantly produced single or multicopy fusion protein has been described, the techniques described above can also be used to add a different polypeptide, peptide and/or amino acid as a biologically added protecting group to the N- and/or C-terminal end of the single or multicopy polypeptide. For example, in the method described above if the binding protein is eliminated, the interconnecting peptide is sufficient itself as a biologically added protecting group. In another example, the biologically added protecting group can be as simple as a single amino acid added to the N- and/or C-terminal amino acids of the single copy polypeptide.

In an alternative version, the single or multicopy polypeptide can be recombinantly produced as a truncated polypeptide having only a portion of the amino acid sequence of the desired polypeptide. The recombinantly produced truncated single or multicopy polypeptide preferably lacks about 1 to about 10 amino acids at the N- or C-terminal end of the molecule. The gene for the truncated single or multicopy polypeptide can be synthesized by automated synthesis or can be obtained by restriction endonuclease cleavage of entire gene sequence so that the coding sequence for up to 10 amino acids is removed. The truncated gene can be combined with the gene sequences for the binding protein and interconnecting peptide or any other biologically added protecting group as described herein. The amino acids missing from the truncated single or multicopy polypeptide are later replaced by modification reaction.

The preferred starting material for the C- and/or N-terminal selective modification method of the present invention is a multicopy fusion protein having several copies of polypeptide tandomly linked and intraconnected via an amino acid and interconnected via a peptide to the binding protein. An example of the preferred multicopy fusion protein is comprised of a human carbonic anhydrase II binding protein interconnected by an enterokinase recognition site to the N-terminal α-amine of a multicopy polypeptide having three tandomly linked copies of the polypeptide mastoparan intraconnected with the amino acid arginine, and having a C-terminal arginine.

An expression cassette for the human carbonic anhydrase mastoparan fusion protein is formed as follows. The especially preferred gene for the human carbonic anhydrase II binding protein is obtained as described in copending application Ser. No. 07/552,810. When employing the hCAII gene, at least a portion representing the functional fragment of the enzyme is modified as follows: (a) the hCAII asparagine-glycine peptide sequence is changed; the asparagine is changed to glutamine or glycine is changed to alanine; and (b) the sequence for the last three terminal amino acids is deleted.

The modified hCAII gene sequence can be inserted into an expression vector which is compatible with *E. coli*. Cleavage of the DNA sequence at a site downstream from the regulatory portion of the vector followed by insertion of the gene through blunt- or sticky-end ligation forms the recombinant vector. The insertion is downstream from the promoter sequences that provide for expression in the host cells. The promoter is preferably the T7 promoter. The T7 promoter is recognized by a chromosomally encoded T7 RNA polymerase induced by isopropyl-thiogalactoside.

A short DNA fragment coding for the interconnecting peptide is inserted near the 3' or 5' end of the intact or partial hCA gene (intraconnecting peptides are discussed below). In a preferred version, the peptide sequence recognized by enterokinase is inserted at the 3' terminal of the carbonic anhydrase.

The gene fused onto the carbonic anhydrase II-enterokinase recognition site construct encodes three copies of the mastoparan sequence separated by Arginine residues (45 amino acids including C-terminal arginine). The amino acid sequence for mastoparan is Ile-Asn-Leu-Lys-Ala-Leu-Ala-Ala-Ala-Leu-Ala-Lys-Lys-Ile-Leu (SEQ ID NO:7). This gene is prepared synthetically by the method of multiple complimentary oligonucleotide synthesis as described by S. Beaucage et al., *Tetra. Letters*, 221:859 (1981), and is designed using optimal codon usage for *E. coli* and contains unique and useful restriction endonuclease sites. The synthetic gene is inserted into the expression vector immediately downstream from the enterokinase recognition site by standard recombinant DNA methodology.

*E. coli* cells are transformed with the expression vector and transformed cells are selected. The expression of the protein in the cells is induced with isopropylthiogalactoside. Once sufficient protein has accumulated, the cells are lysed and the fusion protein purified.

4. Purification of Single or Multicopy Fusion Protein

The recombinant single or multicopy polypeptide produced as a fusion protein allows for easy purification by affinity chromatography. The fusion protein produced in the transformed cells can be soluble in the cells or insoluble in inclusion bodies. Soluble fusion protein is obtained by lysis of the transformed cells to form a crude cell lysate. The crude cell lysate can be further purified by methods including ultrafiltration and ion exchange chromatography before purification by affinity chromatography. Insoluble fusion protein in inclusion bodies is also purified by similar methods.

To perform affinity purification, the crude mixture of materials is combined with an immobilized ligand for the binding protein. Examples of the binding protein, corresponding ligand and dissociation constants are given in Table 2. For the preferred carbonic anhydrase enzyme, the ligand is sulfanilamide or a benzene sulfonamide derivative. Immobilization of the ligand on a solid support can be accomplished by the methods of W. Scouter, *Methods Enzymol.*, 34, 288–294 (1974); S. Marcus, *Methods Enzymol.*, 34, 377–385 (1974); A. Matsura et al., *Methods Enzymol.*, 24, 303–4 (1974); R. Barker, *Methods Enzymol.*, 34, 317–328 (1974); I. Matsumoto, *Methods Enzymol.*, 34, 324–341 (1974), J. Johansen, *Carlsberg Res. Commun.*, 14, 73 (1976) and G. S. Bethell et al., *J. Biol. Chem.*, 254, 2572–2574 (1979); the disclosures of which are incorporated herein by reference. The fusion protein binds to the immobilized ligand through the reversible affinity of the binding protein for its ligand. The remaining constituents and debris of the crude mixture of materials can then be removed by washing or similar techniques.

Two routes can be employed for further purification of the fusion protein. According to the first route, the single or multicopy fusion protein is dissociated intact from the immobilized ligand by washing with a strong competing ligand solution. Examples include cyanides, pseudocyanides such as thiocyanides, perchlorates, halide and similar strong Lewis bases.

According to the second route, the immobilized single or multicopy fusion protein is contacted directly with cleavage reagent to release the single or multicopy polypeptide. To isolate the single or multicopy polypeptide in the second route, its mixture with cleavage enzyme can be combined with a means for molecular weight selection (e.g. partition chromatography dialysis, filtration based on molecular size or high pressure liquid chromatography on a "particle exclusion" base or ion exchange chromatography) such that the high molecular weight cleavage enzyme is separated from the free variable fused peptide. Or, the mixture can be combined with an immobilized affinity material for the cleavage enzyme.

The cleavage enzyme chosen will depend upon the interconnecting peptide chosen. Examples of cleavage enzymes and their cleavage sites are given in Table 1.

The purification methods described above yield the starting materials for the method of the invention: a single copy fusion protein, a multicopy fusion protein, a single copy polypeptide, a multicopy polypeptide, or a truncated single or multicopy polypeptide. In a preferred embodiment, the single and multicopy polypeptides are recombinantly produced from a fusion protein. Both single copy and multicopy polypeptides can be recombinantly produced with additional residues at the N-terminal and/or C-terminal ends of the molecule without the presence of a binding protein or interconnecting peptide.

In a preferred version, the human carbonic anhydrase multicopy mastoparan fusion protein is isolated from cell lysates of transformed *E. coli* by ultrafiltration followed by ion exchange chromatography. The cell lysate material is then loaded onto an affinity column containing sulfanilamide. The bound fusion protein is then released from the affinity column by washing with potassium thiocyanate. The purified fusion material is then digested with enterokinase, and the multicopy polypeptide is purified from the carbonic anhydrase binding protein by ultrafiltration. The purified multicopy polypeptide is composed of 3 copies of the mastoparan intraconnected by arginine residues and has a C-terminal arginine residue and an unprotected N-terminal α-amine and other side chain groups.

B. Cleavage and Reaction of the Starting Materials With Chemical Protecting Agents In order to selectively modify the desired recombinant polypeptide at the N- and/or C-terminal α-carbon reactive groups, the other reactive side chain are protected by reaction with up to three chemical protecting agents. The biologically added protecting group at N- and/or C-terminal α-carbon is cleaved to provide an unprotected reactive N- and/or C-terminal α-carbon group available for modification.

The number and sequence of the cleaving and reacting steps can vary depending on the starting material and modification. In some cases, the reaction scheme is conducted by reacting the starting material with the chemical protecting agent(s) first and then cleaving with a cleavage reagent specific for the N- and/or C-terminal biological protecting group. For example, if the starting material is to be modified at the N-terminal amino acid or if the cleavage site of the biologically added protecting group is present in the desired polypeptide, then the starting material is protected first and cleaved second. In other cases, the starting material is cleaved first and then reacted with up to three chemical protecting agents. For example, for modification at the C-terminal amino acid the starting material is cleaved and then reacted with the chemical protecting agents.

Other variations in the number and sequence of the cleaving and reacting steps are possible. A reaction scheme can be selected according to the factors provided in Table 3.

TABLE 3

| Factor | Present In Starting Material | Method |
|---|---|---|
| 1. Is the cleavage recognition sequence of the biological protecting group present in the amino acid sequences of the polypeptide? | Yes | React with chemical protecting agents and then cleave |
| | No | Can go either way |
| 2. Is the N-terminal amino acid to be modified? | Yes | React with chemical protecting agents, then cleave. |
| | No | Cleave and then react with chemical protecting agents |
| 3. Is the starting material a multicopy fusion protein? | Yes | Two cleavage steps required - one at the inter- and one at the intraconnecting peptides. |
| 4. Are both N- and C-terminal amino acids to be modified? | Yes | Extra steps of cleavage and modification required. |
| 5. Does the modification reaction require protection of reactive side chain groups? | Yes | React with chemical protecting agent before modification. |
| | No | Cleave and then modify. No reaction with chemical protecting agent required. |

Once a particular starting material has been selected and formed, the steps of the reaction scheme can be selected by according to the factors in Table 3.

For example, for N-terminal modification of the preferred multicopy fusion protein, the following reaction scheme is selected. The preferred multicopy fusion protein is three copies of the mastoparan polypeptide intraconnected by arginine residues and interconnected by the enterokinase recognition peptide to carbonic anhydrase and having a C-terminal arginine residue. Neither the sequence for inter- or intraconnecting peptides is found in the single copy polypeptide, so the reaction scheme can go either way. However, since N-terminal modification is desired, the multicopy fusion protein is reacted with a chemical protecting agent before it is cleaved. Since the starting material is a multicopy fusion protein, cleavage will involve reaction with a cleavage enzyme specific for the interconnecting peptide and the intraconnecting peptide which in this case are different. Only the N-terminal α-carbon is to be modified so after the cleavage step no additional cleavage or modification reactions are necessary. The modification reaction is N-terminal acetylation reaction requiring protection of the reactive side chain groups. The final product is mastoparan having N-terminal acetyl group. This reaction scheme can be depicted as follows:

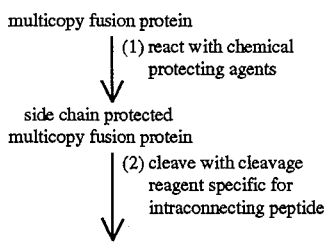

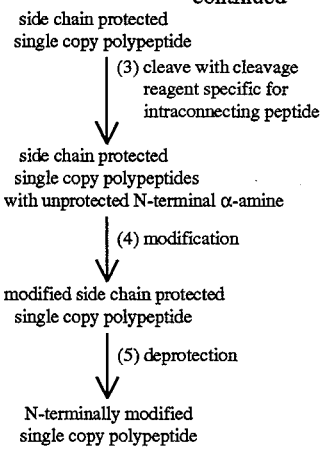

1. Protection of Reactive Side Chain Groups with Chemical Protecting Agents: Amine, Hydroxyl, Carboxyl, Thiol Protection The purified single or multicopy fusion protein and the single or multicopy polypeptide also contain amino acids with side chains having reactive groups like ε-amine, hydroxyl, carboxyl and thiol groups. In addition, one of the terminal amino acid α-carbon reactive groups can also be unprotected. In order to provide for the selective modification at the N-terminal α-amine and/or C-terminal α-carboxyl groups, these other reactive groups are protected so that they are unavailable to react with the modifying agent.

The purified single or multicopy fusion protein and the single or multicopy polypeptide are reacted with up to three chemical protecting agents. The protecting agent is selected by the capacity to form a protecting group at a particular type of side chain reactive group, as will be described herein. More than one protecting agent can be used depending on the different types of side chain reactive groups present in the single copy polypeptide.

Preferably, the single copy polypeptide is selected in part because it has a limited number of different side chain reactive groups to minimize the number of chemical protecting agents that are employed. For example, preferably, the single copy polypeptide is mastoparan which contains ε-amine and hydroxyl groups as reactive side chain groups.

a. Amine Protection

A single or multicopy recombinant polypeptide having at least one reactive amine group is reacted with a chemical protecting agent to form an amine specific protecting group. Preferably, the single or multicopy polypeptide only contains ε-amino reactive side group chains. The second protecting agent acts on α-amine as well as ε-amine side chain groups like those found in lysine to form a stable but reversible bond. The bond formed between the amine group and the protecting group is sufficiently stable to withstand the chemical modifying reaction conditions but also is easily reversible to allow for deprotection and regeneration of the original amine group.

Suitable chemical protecting agents that form amine protecting groups can be selected by identifying protecting groups that form a less stable bond with the unprotected groups as compared with the stability of a bond, like an amine, formed at α-carboxyl of the C-terminal amino acid or the N-terminal α-amine. The chemical protecting agents form bonds at unprotected amine or hydroxyl groups that are less stable than and are different from the biological protecting group at the N- and/or C-terminal that are typically a polypeptide, peptide or an amino acid. Although not meant to limit the invention, the protecting group can be selected by identifying protecting group substituents that will stabilize the formation of a carbonium ion on the protecting group relative to the carbonium ion formed at the C-terminal α-carboxyl group. Substituents containing aromatic groups, oxygen, nitrogen, unsaturated groups, aromatic acetyl groups, carbamates, and cyclic anhydrides are groups that can act to stabilize the carbonium ion on the "leaving protecting group" and act to form a stable but reversible bond with amine.

Suitable chemical protecting agents include alkyl, alkoxy or aryl carbamating agents, alkyl or aryl substituted acylating agents, and alkyl, alkoxy or aryl substituted anhydrides and aryl or unsaturated cyclic anhydrides. The order of preference of the protecting group is as follows: aryl or unsaturated cyclic anhydrides >carbamates>stabilized single acids.

Specific examples of amine protecting groups include N-trichloroacetyl, N-trifluoroacetyl, N-o-nitrophenylacetyl, N-o-nitrophenoxyacetyl, N-acetoacetyl, N-3-phenylpropionyl, N-3-(p-hydroxyphenyl)propionyl, N-2-methyl-2-(o-nitrophenoxy)propionyl, N-2-methyl-2-(o-phenylazophenoxy)propionyl, N-4-chlorobutyryl, N-o-nitrocinnamoyl, N-picolinoyl, N-(N'-acetylmethionyl), N-benzoyl, N-phthaloyl, and N-dithiasuccinoyl.

Suitable examples of carbamate protecting groups (including the amine) include methyl carbamate; N-fluorenylmethyl carbamate; 2,2,2-trichloroethyl carbamate; 2-trimethylsilylethyl carbamate; 1,1-dimethylpropynyl carbamate; 1-methyl-1-phenylethyl carbamate; 1-methyl-1-(4-biphenylyl)ethyl carbamate; 1-dimethyl-2-haloethyl carbamate; 1,1-dimethyl-2-cyanoethyl carbamate; t-butyl carbamate; cyclobutyl carbamate; 1-methylcyclobutyl carbamate; 1-adamantyl carbamate; vinyl carbamate; allyl carbamate; cinnamyl carbamate; 8-Quinolyl carbamate; N-hydroxypiperidinyl carbamate; 4,5-diphenyl-3-oxazolin-2-one; benzyl carbamate; p-nitrobenzyl carbamate; 3,4-dimethoxy-6-nitrobenzyl carbamate; 2,4-dichlorobenzyl carbamate; 3-benzisoxazolylmethyl carbamate; 9-anthrylmethyl carbamate; diphenylmethyl carbamate; isonicotinyl carbamate; s-benzyl carbamate; and N-(N'-phenylaminothiocarbonyl) derivative.

Other amine protecting groups include N-allyl, N-phenacyl, N-3-acetoxypropyl, quatenary ammonium salts, N-methoxymethyl, N-benzyloxymethyl, N-pivaloyloxymethyl, N-tetrahydropyranyl, N-2,4-dinitrophenyl, N-benzyl, N-o-nitrobenzyl, N-di(p-methoxyphenyl)methyl, N-triphenylmethyl, N-(p-methoxyphenyl)diphenylmethyl, N-diphenyl-4-pyridylmethyl, N-2-picolyl-N'-oxide, N,N'-isopropylidine, N-benzylidene, N-p-nitrobenzylidene, N-salicylidine, N-(5,5-dimethyl-3-oxo-1-cyclohexenyl), N-nitro, N-oxide, N-diphenylphosphinyl, N-dimethylthiophosphinyl, N-benzenesulfenyl, N-o-nitrobenzenesulfenyl, N-2,4,6-trimethylbenzenesulfenyl, N-toulenesulfonyl, N-benzylsulfonyl, N-trifluromethylsulfonyl, and N-phenacylsulfonyl.

Especially preferred protecting agents of the invention are maleic or citraconic anhydrides.

Typically, the amine groups can be protected by formation of an amide bond by the reaction of the amine groups with an anhydride as follows:

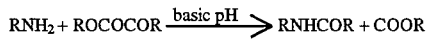

The reaction is conducted under conditions that favor the formation of a reversible, stable amide bond, preferably at the unprotected α-amine group of the N-terminal amino acid and the ε-amine group of lysine. Typically, arginine and histidine are much less reactive.

Amine protection with carbamates proceeds by the reaction of the amine groups as follows:

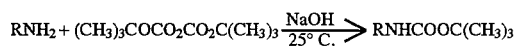

The reaction conditions are also chosen so that the unprotected N-terminal α-amine and lysine ε-amine groups are protected. Typically, arginine and histidine are relatively unreactive.

Polypeptide amine groups can also be protected by addition of other types of groups including N-alkylation or arylation. For example, reaction of amines with diazo compounds in the presence of boron trifluoride results in N-alkylation of the amine groups.

The selection of reaction conditions depends upon the polypeptide amino acid composition, the type of protecting groups added and the modifying agent chosen. Specific conditions and reagents for adding protecting groups to amine groups are described in *Protective Groups in Organic Chemistry*, T. Green, editor, John Wiley and Sons (1988), which is hereby incorporated by reference.

b. Protection of the Amino Acids Having Hydroxyl Side Chains

A preferred single or multicopy recombinant polypeptide or fusion protein useful in the method of the invention has one or two different types of reactive side chain groups, including amino acids having hydroxyl side chains. For example, a polypeptide can contain α-amine, ε-amine and hydroxyl groups as reactive groups. The method of the invention provides for protection of amine and hydroxyl reactive side chain groups.

The hydroxyl groups of the single or multicopy polypeptide are protected by reacting the polypeptide with the chemical protecting agent as described for amine protection. The chemical protecting agent forms a stable reversible bond at the side chain hydroxyl group in the same manner as described for amine protection. The bond formed between the hydroxyl group and the protecting group is sufficiently stable to withstand the chemical modifying reaction conditions but is also easily reversible to allow for deprotection and regeneration of the original hydroxyl group.

Suitable second protecting agents are the same as described for amine protection including alkyl, alkoxy or aryl carbonating agents, alkyl or aryl substituted acylating agents, alkyl, alkoxy or aryl substituted anhydrides, aryl or unsaturated cyclic anhydrides. The preferred protecting groups (including the hydroxyl oxygen) that form a stable but easily reversible bond are, in order of preference, aryl or unsaturated cyclic anhydrides greater than carbamates, greater than stabilized single acids.

Specific examples of the protecting groups are provided in the amine protection section herein. The highly preferred amine and hydroxyl protecting agent is maleic anhydride.

Alternatively, hydroxyl group protection can be achieved by reacting the starting material with a protecting agent that forms an ether or ester bond at the hydroxyl side chain groups. The ether or ester bonds formed are stable to the modifying conditions but are readily reversible to provide for regeneration of the original hydroxyl group.

Specific examples of hydroxyl protecting groups include the following ethers: methyl ether; methoxymethyl ether (MOM); methylthiomethyl ether (MTM); 2-methoxyethoxymethyl ether (MEM); Bis(2-chloroethoxy) methyl ether; tetrahydropyranyl ether (THP); tetrahydrothiopyranyl ether; 4-methoxytetrahydropyranyl ether; 4-methoxytetrahydrothiopyranyl ether; tetrahydrofuranyl ether; tetrahydrothiofuranyl ether; 1-ethoxyethyl ether; 1-methyl-1-methoxyethyl ether; 1-(phenylselenyl)ethyl ether; t-butyl ether; allyl ether; benzyl ether; o-nitrobenzyl ether; triphenylmethyl ether; α-naphthyldiphenylmethyl ether; p-methoxyphenyldiphenylmethyl ether; 9-(9-phenyl-10-oxo)anthryl ether (Tritylone); trimethylsilyl ether (TMS); isopropyldimethylsilyl ether; t-butyldimethylsilyl ether (TBDMS); t-butyldiphenylsilyl ether; tribenzylsilyl ether; and triisopropylsilyl ether.

Specific examples of hydroxyl protecting groups include the following esters: formate ester; acetate ester; trichloroacetate ester; phenoxyacetate ester; isobutyrate ester; pivaloate ester; adamantoate ester; benzoate ester; 2,4,6-trimethylbenzoate (mesitoate) ester; methyl carbonate; 2,2,2-trichloroethyl carbonate; allyl carbonate; p-nitrophenyl carbonate; benzyl carbonate; p-nitrobenzyl carbonate; S-benzyl thiocarbonate; N-phenylcarbamate; nitrate ester; and 2,4-dinitrophenylsulfonate ester.

c. Protection of β- or γ- Carboxyl Groups

The single copy or multicopy polypeptide or fusion protein can also have amino acids with β- or γ-carboxyl side chains. The β- or γ-carboxyl side chains can be protected with a chemical protecting agent that reacts with carboxyl groups to form a stable but reversible bond. The bond formed between the β- or γ-carboxyl groups is sufficiently stable to withstand chemical modifying conditions at the α-carboxyl group but is also easily reversible to allow for deprotection and regeneration of the original β- or γ-carboxyl group. The protection conditions for protecting carboxyl groups are also selected so that the amine and/or hydroxyl protecting groups are not adversely affected.

Suitable protecting agents for protecting a carboxyl groups include o-nitrophenol esters, alkyl or benzyl esters, 1-hydroxybenzotriazol esters, alkylchlorocarbonates, azides and hydrazides. The especially preferred agent for the protection of carboxyl groups is o-nitrophenol.

Specific examples of carboxyl protecting groups include the following esters, amides and hydrazides: methyl ester; methoxymethyl ester; methylthiomethyl ester; tetrahydropyranyl ester; benzyloxymethyl ester; phenacyl ester; N-phthalimidomethyl ester; 2,2,2-trichloroethyl ester; 2-haloethyl ester; 2-(p-toluenesulfonyl)ethyl ester; t-butyl ester; cinnamyl ester; benzyl ester; triphenylmethyl ester; Bis(o-nitrophenyl)methyl ester; 9-anthrylmethyl ester; 2-(9,10-dioxo)anthrylmethyl ester; piperonyl ester; trimethylsilyl ester; t-butyldimethylsilyl ester; S-t-butyl ester; 2-alkyl-1,3-oxazolines; N,N-dimethylamide; N-7-nitroindoylamide; hydrazides; N-phenylhydrazide; N,N'-diisopropylhydrazide.

The preferred α-carboxyl protecting agent can act at the α- as well as the β- or γ-carboxyl groups to form active esters. Selective modification like amidation of the α-carboxyl groups can be achieved by one of two methods. Protection of the β- or α-carboxyl group can be a separate step, after the reaction of the single or multicopy polypeptide with the first protecting agent. Alternatively, protection of the β- or α-carboxyl group can occur during the modification step.

In the first method, the protection of β- or α-carboxyl groups is accomplished in a separate step, typically after the amine and hydroxyl groups have been protected with the first chemical protecting agent. The single or multicopy peptide has an additional C-terminal amino acid such as arginine. The additional C-terminal amino acid residue acts to protect the α-carboxyl group of the penultimate amino acid. The protected single or multicopy polypeptide with the C-terminal arginine residue is reacted with the second agent to add protecting groups to the β- or γ-carboxyl groups as well as the α-carboxyl group of the arginine. The arginine group is removed by digestion with carboxypeptidase B leaving a single or multicopy peptide with protected β- or γ-carboxyl groups and an unprotected C-terminal α-carboxyl group. The unprotected C-terminal α-carboxyl group is then selectively amidated with the chemical amidating agent.

In the second method, the β- or γ- or α-carboxyls are protected in the modification reaction. Selective α-carboxyl modification occurs by selecting conditions that favor the more reactive α-carboxyl group relative to the β- or γ-carboxyl groups. For example, when the carboxyl groups are protected by forming active esters, selective amidation occurs at the α-carboxyl group by the addition of stoichiometric amounts of ammonia at a pH of a 6 to 7. While not in any way meant to limit the invention, the difference in the pKa values between the α-ester and β- or γ-esters allows for the selective amidation at the α-carboxyl.

d. Thiol Protection

A single or multicopy recombinant polypeptide having at least one reactive side chain thiol group is reacted with a chemical protecting agent to form a thiol-specific protecting group. The bond formed between the thiol group and the protecting group is sufficiently stable to withstand the chemical modifying conditions, but is also easily reversible to allow for deprotection and regeneration of the original thiol group.

Specific examples of thiol protecting groups include S-benzyl thioether, S-p-methoxybenzyl thioether, S-p-nitrobenzyl thioether, S-4-picolyl thioether, S-2-picolyl N-oxide thioether, S-9-anthrylmethyl thioether, S-diphenylmethyl thioether, S-Di(p-methoxyphenyl)methyl thioether, S-triphenylmethyl thioether, S-2,4-Dinitrophenyl thioether, S-t-butyl thioether, S-isobutozymethyl hemithioacetal, S-2-tetrahydropyranyl hemithioacetal, S-acetamidomethyl aminothioacetal, S-cyanomethyl thioether, S-2-nitro-1-phenylethyl thioether, S-2,2-Bis (carboethoxy)ethyl thioether, S-benzoyl derivative, S-(N-ethylcarbamate), and S-ethyl disulfide. The preferred thiol protecting agent is acetic anhydride in potassium bicarbonate $(CH_3CO_2)O/KHCO_3$.

Typically, the thiol groups can be protected by formation of a thioether bond as follows:

or

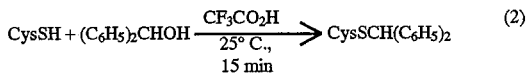

The reaction is conducted under conditions that favor the formation of a reversible stable thioether bond. Typically, methionine is not reactive under these conditions.

Alternatively, thiol groups can be protected by formation of a thioester bond as follows:

The single copy or multicopy polypeptide can be transferred into an organic solvent such as dimethylformamide, if necessary. Other reactive side chain group are not adversely affected by these reaction conditions.

The selection of reaction conditions depends upon the single copy polypeptide amino acid composition, the type of protecting groups added, and the modifying agent chosen. Specific conditions and reagents for adding protecting groups to thiol groups are described in *Protective Groups in Organic Chemistry*, T. Greene, editor, John Wiley and Sons (1988), which is hereby incorporated by reference.

2. Cleavage of the Biological Protecting Group

The biological protecting group is cleaved to generate an unprotected N- or C-terminal α-carbon reactive group. The cleavage step can take place either before or after the reaction of the starting material with the chemical protecting agents. In the preferred embodiment, cleavage occurs after protection of the side chain reactive groups with the protecting agents. The cleavage step can require more than one cleavage reagent to generate the unprotected N- or C-terminal α-carbon reactive group. The unprotected C- or N-terminal α-carbon reactive groups are available for modification.

The cleaving reagent is an enzyme or chemical reagent that cleaves at the recognition sequence of the inter- or intraconnecting peptide or removes intraconnecting amino acids from the N- or C-terminal end. Specific example of the enzymes and chemical cleavage reagents specific for inter- or intraconnecting peptides are provided in Table 1. Enzymes that remove amino acid residues from the C-terminal end are carboxypeptidases and include carboxypeptidase A, carboxypeptidase B, carboxypeptidase Y, and carboxypeptidase K. Enzymes that remove residues from the N-terminal end are aminopeptidases, and include leucine aminopeptidase, amino peptidase M, Aeromonas aminopeptidase, X-prolyl dipeptidyl amino peptidase, as well as enzymes listed in Table 1.

A single cleavage reagent can be sufficient but multiple cleavage reagents may be necessary to provide an unprotected N- or C-terminal α-carbon reaction group. The inter- or intraconnecting peptide can contain multiple cleavage sites and preferably has at least one enzymatic cleavage site and one chemical cleavage site. In site-specific cleavage, amino acid residues of the inter- or intraconnecting peptide can remain at the N- or C-terminal ends and require removal by carboxy- or aminopeptidase enzymatic digestion.

Multiple cleavage reagents and steps can also be required depending on the selection of the starting material. For example, if the starting material is a multicopy fusion protein, cleavage with a cleavage reagent specific for the inter- and intraconnecting peptide generates a mixture of single copy polypeptides. Preferably the interconnecting and intraconnecting peptide have a sequence that is recognized by the same cleavage reagent so single copy polypeptides can be generated in a single step using a single cleavage reagent. If the interconnecting and intraconnecting peptides are different, two different cleavage enzymes can be employed together or sequentially to generate the single copy polypeptides. The mixture of single copy polypeptides contain single copy polypeptides having intraconnecting peptide at the C-terminal end. If modification is to be made at the C-terminal α-carboxyl group, the mixture is also cleaved with a carboxypeptidase to remove the intraconnecting peptide at the C-terminal end.

Multiple cleavage steps can be required if both the N- and C-terminal α-carbon reactive groups are to be modified. For example, a recombinant single copy polypeptide protected at both the N- and C-terminal ends with biological protecting groups is sequentially cleaved. Typically, the N-terminal biological protecting group is removed and the N-terminal α-amine group is then modified. The C-terminal protecting group is then removed and the C-terminal α-carboxyl group is then modified. In this case, the N- and C-terminal biological protecting groups contain different recognition sequences for cleavage reagents to allow for sequential cleavage.

In a preferred version, the recombinant multicopy fusion protein having three copies of the mastoparan polypeptide intraconnected by arginine residues and interconnected by enterokinase recognition peptide sequence to carbonic anhydrase and with a C-terminal arginine is cleaved to form single copy polypeptides by sequential cleavage. The multicopy fusion protein is cleaved with enterokinase to produce a multicopy polypeptide. The multicopy polypeptide is then reacted with maleic anhydride which adds a protecting group to unprotected ε-amino groups of lysine present in the mastoparan polypeptide. The multicopy polypeptide is then cleaved with trypsin to produce a mixture of single copy polypeptides. The protected lysine groups are not recognized and cleaved with trypsin. The mixture of single copy polypeptides contains single copy polypeptides with unprotected N-terminal α-amine groups and intraconnecting peptide at the C-terminal α-carboxyl group. If the C-terminal α-carboxyl group is to be modified, the unprotected N-terminal α-amine is protected by reaction with a chemical protecting agent, like maleic anhydride and the C-terminal intraconnecting peptide residues are removed by cleavage with a carboxypeptidase. The side chain protected single copy polypeptide with unprotected C-terminal α-carboxyl produced can then be modified.

C. Selective Modification of N-Terminal α-Amine and/or C-Terminal α-Carboxyl Groups.

Recombinant polypeptides or peptides can be modified selectively at the N-terminal or C-terminal α-carbon reactive groups by the addition of a variety of organic moieties. While not in any way meant to limit the invention, modification reactions at the C-terminal α-carboxyl or N-terminal α-amine groups are those that proceed by nucleophilic substitution. Nucleophilic substitutions are described in *Advanced Organic Chemistry*, in Chapter 10, 3rd ed., John Wiley and Sons, editor, NY (J. March 1984), which is hereby incorporated by reference. The bonds formed at the N- and/or C-terminal α-carbon reactive groups are stable and generally irreversible under the deprotection conditions employed to regenerate the side chain groups. Polypeptides can be sequentially modified at the N- and C-terminal α-carbon reactive group by the same or different modifications.

Specific examples include addition to or replacement of terminal amino acids with a D-amino acid, D-amino acid containing peptide, L-amino acid peptide, or an amino acid analogue or derivative at one or both of the terminal ends of the recombinant polypeptide by formation of an amide bond. Another modification is the conversion of an N-terminal glutamic acid or glutamine to a pyroglutamyl residue. The preferred modification of the method of the invention is the selective C-terminal α-carboxyl amidation reaction.

The modification made to the N-terminal and/or C-terminal α-carbon reactive group can be selected according to several factors. Factors to be considered in selecting the terminal modifications are the amino acid sequence of the single copy polypeptide, the size of the single copy polypeptide, the change in the biological activity of the single copy polypeptide, how the modified single copy polypeptide is going to be used, and prevention of racemization at the modified N- and/or C-terminal α-carbon.

The amino acid sequence of the single copy polypeptide preferably has about one or two different reactive side chain groups. For example, a polypeptide having an ε-amine and hydroxyl side chain groups can be protected in a single step using an amine protecting agent as described previously. The modifications, conditions and agent are chosen so that the ε-amine and hydroxyl groups are not deprotected or otherwise adversely affected during the modification reaction. In contrast, a single copy polypeptide with both ε-amine, hydroxyl, β- or γ-carboxyl, and thiol groups can require reaction with three different protecting agents to provide for side chain protection of the ε-amine and hydroxyl groups, β- or γ-carboxyl groups, and thiol groups. The modification conditions and reactions are selected so that the side chain protecting groups remain intact and are not adversely affected.

Conditions that lead to deprotection of the amine, carboxyl and thiol protecting groups are described in *Protecting Groups in Organic Synthesis,* T. Green, editor, John Wiley and Sons (1988). These conditions should be avoided during the modification process and, thus, the modification reaction conditions should be chosen to avoid or prevent deprotection of these side chain reactive groups.

The size of the single copy polypeptide is preferably about 10–50 amino acids. While the selective modification methods of the invention can be conducted on larger polypeptides, reaction conditions for adding protecting groups and modifying groups are selected so as not to cause irreversible denaturation of the polypeptide. Polypeptides with greater than 50 amino acids are protected and modified in aqueous solutions of a pH of about 2–10 and a temperature of less than about 50° C.

Modifications to the polypeptide can change the biological activity of the polypeptide. For example, C-terminal amidation of many small peptides, like mastoparan or the human gastrin releasing peptide, enhances the biological activity of these peptides. Moreover, addition of peptide sequences of D or L-amino acids can provide for targeting of the polypeptide to a specific cell type, decreasing the rate of breakdown and clearance of the peptide, increasing the biological potency and adding other biological activities to the polypeptide. Addition of D-amino acids or peptides or derivatives of amino acids can also result in the formation of antagonists. The choice of modification can be made upon the desired change of the biological activity of the peptide.

The fourth factor to consider in selecting modifying reactions and conditions is how the modified product is going to be used. If the polypeptide is to be used in vivo, the modification selected can be one that enhances, targets, expands, or inhibits the biological activity of the polypeptide. If the polypeptide is being modified for use in a diagnostic test, the impact of the modification on the structure of the polypeptide rather than the biological activity is examined. For use in diagnostic tests, the modified polypeptide is still specifically recognized by antibodies or by specific binding to a target molecule.

The fifth factor to consider in choosing the modification reaction and conditions is to prevent formation of a racemic mixture of the modified single copy polypeptides. Some types of modification reactions are known to result in racemic mixtures and, thus, are not suitable for the method of the present invention.

Specific examples of modification reactions and conditions follow.

1. Selective Amidation of the Carboxy-Terminal Amino Acid

The protected single copy polypeptide having unprotected C-terminal α-carboxyl group is reacted with a chemical amidating agent by standard methods, as described in Bodanszky, *Peptide Chemistry: A Practical Textbook,* Springer-Varlag, publisher (1988), which is hereby incorporated by reference. Suitable chemical amidating agents include 1-ethyl-3-(3-dimethyl-aminopropyl) ethyl carbodiimide hydrochloride and ammonia, water soluble carbodiimides and ammonia, dicyclohexyl carbodiimide and ammonia, acid chlorides and ammonia, azides and ammonia, mixed anhydrides and ammonia, methanolic HCl and ammonia, o-nitrophenyl esters and ammonia and esters of 1-hydroxybenzotrazole and ammonia.

Typically, the protected polypeptide is reacted with a chemical amidating agent like carbodiimide and o-nitrophenol to form activated esters as follows:

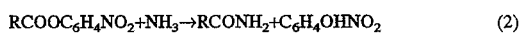

$$RCOOH + C_6H_5CNCC_6H_5 + C_6H_4OHNO_2 \rightarrow RCOOC_6H_4NO_2 \quad (1)$$

$$RCOOC_6H_4NO_2 + NH_3 \rightarrow RCONH_2 + C_6H_4OHNO_2 \quad (2)$$

The amidation occurs upon addition of ammonia or a source of ammonia to the active ester. Other carboxyl or acidic side chains present in the polypeptide, if not already also protected, form active esters. In order to provide for a selective α-carboxyl C-terminal amidation, reaction conditions are chosen to favor amidation at the more reactive α-carboxyl in contrast to the β- or γ-carboxyl side chains. For example, addition of a stoichiometric amount of ammonia at a pH of about 6 favors the formation of the amide at the α-carboxyl group. Carboxyl activating and amidation conditions are also such that deprotection of the amine hydroxyl groups does not occur.

An alternative method of amidation is to react the unprotected C-terminal α-carboxyl group with the photonucleophile o-nitrophenol-glycineamide. The photonucleophile acts to convert the carboxyl group to the amide.

The selection of reaction conditions depends upon the amino acid composition of the polypeptide, the type of protecting group utilized, and the chemical amidating agent chosen. For example, if the polypeptide does not contain β- or γ-carboxyl groups, the utilization of conditions favoring α-carboxyl amidation is not necessary.

The preferred side chain protected mastoparan polypeptide is reacted with 1-ethyl-3-(3-dimethylaminopropyl) ethyl carbodiimide hydrochloride in the presence of excess $NH_4OH$ to form a C-terminal amidated protected mastoparan polypeptide. Since mastoparan does not contain aspartic or glutamic acid, reaction conditions are not adjusted to favor amidation of the α-carboxyl group. The C-terminal amidated protected polypeptide is then deprotected and purified.

2. Modification of N-terminal and C-terminal Amino Acid With D-amino Acids or Peptides, L-Amino Acid Peptides, and Amino Acid Derivatives A D-amino acid, L-amino acid, an amino acid derivative, or peptides containing a combination thereof can be added to the N-terminal and/or C-terminal α-carbon reactive group of the protected single copy polypeptide by transamidation or by segment condensation reaction. Alternatively, the D-amino acid, L-amino acid, amino acid derivative or peptides containing a mixture thereof can replace the N-terminal or C-terminal amino acid or amino acids of a portion of a side chain protected recombinant single copy polypeptide.

Typically, a D-amino acid, L-amino acid, amino acid derivative, or peptide can be added by well known solution or solid phase peptide synthesis, as described in *Solid Phase Peptide Synthesis*, 2nd Edition, J. M. Steward and J. D. Young, editors, Pierce Chemical Co., Rockford, Ill. (1984), which is incorporated herein by reference. One example of such a reaction is adding a urethane blocked amino acid to the free N-terminal α-amine of the side chain protected single copy polypeptide in the presence of carbodiimide, mixed anhydrides or active esters. The reaction scheme is represented as follows:

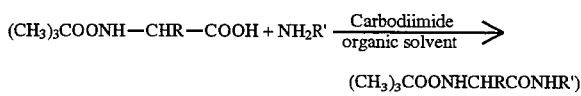

An alternative synthesis is the segment condensation procedure, which is preferably used when small peptides are coupled to the N-terminal α-amine groups as described by F. Finn et al., in *The Proteins*, 3rd ed., Neurath and Hill, editors, Academic Press, NY, Vol. 2, pp. 105–253 (1976), which is hereby incorporated by reference.

Replacement of the N-terminal amino acid(s) can be accomplished by removing the N-terminal amino acid or amino acids by cleavage with a chemical or enzymatic cleavage reagent like those provided in Table 1 or with an amino or carboxypeptidase. Alternatively, the recombinantly produced single copy polypeptide can be produced so that gene sequence lacks the codons for the N-terminal or C-terminal amino acid or amino acids. The protected single copy polypeptide preferably lacking up to about 10 N-terminal amino acids can be modified by the addition of a D-amino acid, L-amino acid, amino acid derivative, or peptide containing a mixture thereof as described above.

A specific example includes replacement of the two N-terminal amino acids of ovine β-endorphin with a dipeptide Tyr-D-Ala. The naturally occurring ovine β-endorphin has 31 amino acids. The starting material for the recombinantly produced peptide is a multicopy polypeptide fusion protein containing multicopies of a truncated β-endorphin (amino acids 3–31) intraconnected by arginine.

leutinizing releasing factor (LRF), modified N-terminal of LRF with Ac-D-Phe[1] and/or PCl-D-Phe[2], N-terminal pyroglutamyl residue to litorin, D-alanine at the 2-position of enkephalin, C-terminal modification adding methioninol sulfoxide at the C-terminal of enkephlin, and α and γ endorphin amides. Other analogs of biologically active peptides are described in *Kirk-Othmer Chemical Encyclopedia*, 12:603–617, which is hereby incorporated by reference. The preferred modification is the additional of a D-amino acid at the C-terminal or N-terminal end of the protected single copy polypeptide.

Specific examples of derivatives of amino acids that can be added to or replace terminal amino acids include pyroglutamyl residues, homoserine, hydroxyproline, 3-methylhistidine, hydroxylysine, desmosine, N-methylglycine, N-methylisoleucine, and N-methylvaline.

3. Formation of N-Terminal Acetyl Groups

Naturally occurring polypeptides and analogues can have N-terminal acetyl groups. The modification reaction providing for N-terminal acetyl groups involves reaction of a protected single copy polypeptide with an unprotected N-terminal α-amine group with acetic anhydride as follows:

$$NH_2CR_1COOR_2+(CH_3CO)_2O \rightarrow CH_3CONHCR_1COOR_2 + CH_3COOH$$

An example of an analogue that has an acetylated N-terminal amino acid is an LRF antagonist.

D. Deprotection

The side chain protected modified polypeptide is then deprotected using a variety of conditions depending upon the particular protecting group involved. Deprotection involves removal of the protecting group and regenerating the original reactive group without undesirable side reactions. Deprotection conditions do not adversely affect the N- and/or C-terminal modification.

The deprotection conditions chosen will depend on the type of protecting group. For example, amide and carbamate protecting groups can be removed by incubation under acidic condition of a pH ranging from about 1–4. Other conditions allowing for the removal of the amine and

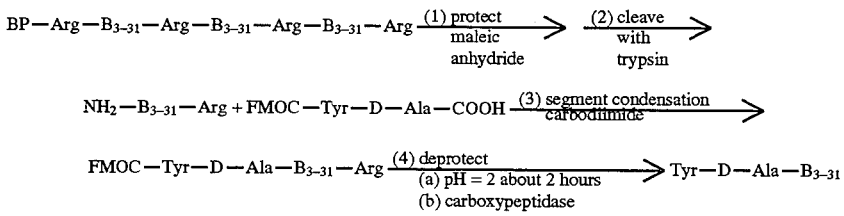

Key
BP—Arg—B$_{3-31}$—Arg—B$_{3-31}$—Arg—B$_{3-31}$—Arg = multicopy fusion protein composed of binding protein (BP) interconnected by Arg to multiple copies of truncated β-endorphin (B$_{3-31}$) intraconnected by arginine
NH$_2$—B$_{3-31}$—Arg = single copy truncated ovine β-endorphin with C-terminal arginine and unprotected N-terminal α-amine
FMOC—Tyr—D—Ala = dipeptide protected at N-terminal with FMOC (9-fluorenylmethyloxycarbonyl)
FMOC—Tyr—D—Ala—B$_{3-31}$—Arg = N-terminal modified protected β-endorphin
Tyr—D—Ala—B$_{3-31}$ = N-terminally modified β-endorphin Specific examples of the types of modifications made to biologically active peptides include addition of L-N-(2-oxopiperidine-6-ylcarbonyl)-L-histidyl-L-thiazolidine-4-carboxamide to thyroliberin (TRF), 3-methylhistidine to TRF, modified C-terminal des-Gly$^{10}$-Pro$^9$-N-ethylamide to hydroxyl protecting groups without undesirable side reactions are described in *Protective Groups in Organic Chemistry*, cited supra.

Specific examples of the cleavage of the amine and hydroxyl protecting groups include the following reactions:

Cleavage of carbamates:

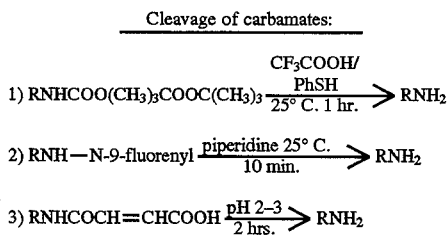

Carboxyl protecting groups can be removed by incubation at a high pH of about 8–11. Other conditions for removal of carboxyl protecting groups without undesirable side reactions are described in *Protective Groups in Organic Chemistry*, cited supra. Specific examples of the cleavage of carboxyl protecting groups include the following reactions:

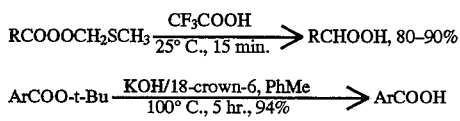

Thiol protecting groups can be removed in the presence of Na and $NH_3$. Other conditions for removal of thiol protecting groups are described in *Protective Groups in Organic Chemistry*, cited supra.

Specific examples of the cleavage of thiol protecting groups include the following reactions:

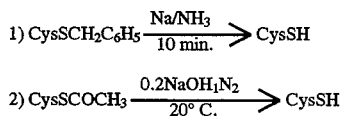

In addition, the modified side chain protected polypeptide can also have the intraconnecting peptide residues at the C- or N-terminal end. If the intraconnecting residues were not removed at an earlier point in the reaction scheme, they can be digested and removed with a cleavage enzyme, like a carboxy or aminopeptidase.

If the side chain protected single copy polypeptide has more than one type of protecting group present, like for example an amine protecting group and carboxyl protecting group, deprotection can be conducted so that the protecting groups are removed sequentially. For example, the amine and hydroxyl protecting groups can be removed by incubation at a pH of about 2 for 2 hours. Then the carboxyl protecting groups can removed by incubating at a pH of about 8–11 for 2 hours. Other combinations of deprotection conditions can be utilized to remove protecting groups from the reactive side chains to regenerate the original reactive group.

After deprotection, the final product is a single copy polypeptide with a modified C- and/or N-terminal amino acid. The final product can be purified by standard methods including size exclusion, ion exchange, or affinity chromatography. In a preferred version, a small peptide like mastoparan can be purified by size exclusion column or HPLC chromatography.

The invention has been described with reference to various specific and preferred embodiments and techniques. However, it should be understood that many variations and modifications can be made while remaining within the spirit and scope of the invention.

EXAMPLE 1

Formation of a C-Terminal α-Amide Polypeptide from a Recombinant Multicopy Fusion Protein Having C-terminal Arginine Groups An expression vector that has a recombinant gene encoding a multicopy fusion protein is formed by standard recombinant DNA methodologies. Briefly, the gene for human carbonic anhydrase is modified by removal of the nucleotide sequence for the three C-terminal amino acids. The gene encoding a multicopy polypeptide containing three copies of a mastoparan polypeptide intraconnected by arginine residues and having a C-terminal arginine is synthesized by automated techniques. The automated techniques are described generally by S. Beaucage et al., *Tetra. Letters*, 221:859 (1981) which is hereby incorporated by reference. The synthesis of the multicopy mastoparan polypeptide with C-terminal arginine (45 amino acids) is conducted using optimal codon usage for *E. coli* and results in a multicopy polypeptide having useful restriction endonuclease sites. The DNA sequence for the interconnecting peptide containing enterokinase recognition sequence (Val-Asp-Asp-Asp-Lys) (SEQ ID NO:8) is synthesized by the automated methods as described above.

The gene for human carbonic anhydrase is inserted in a plasmid downstream from a T7 promoter by standard methods generally known in the art and described by Sambrook et al., cited supra. The DNA sequence for the interconnecting peptide is inserted downstream from the carbonic anhydrase gene. The gene encoding a multiple copy of the mastoparan polypeptide is inserted immediately downstream from the sequence for the interconnecting peptide.

Typically DNA sequences are inserted by restriction endonuclease digestion and ligation as described herein. A 0.5 to 2 mg sample of plasmid DNA is digested in 20 ml of a 1× restriction buffer with 1 to 20 units of restriction enzyme. The reaction mix is incubated for 1 to 16 hours at the temperature recommended by the enzyme supplier. The linearized vector can then be dephosphorylated with calf intestinal phosphatase or bacterial alkaline phosphatase under conditions known to those with skill in the art, e.g. suggested by the supplier. The DNA is then further purified by standard procedures (See Sambrook et al., cited supra) which usually involve a phenyl extraction and ethanol precipitation.

The DNA segment to be inserted is then mixed in a 3 to 5 fold (for large fragments) or 20 to 30 fold (for short oligonucleotides) molar excess precut cloning vector. The ligation is performed in a 1× ligation buffer (20 mm tris pH 7.6, 10 mm magnesium chloride, 0.4 mm β-mercaptoethanol, 0.4 to 1 m ATP), in the presence of T4 DNA ligase at 16° C. for 16 hours. The same procedure is repeated successively to add DNA segments successively and the restriction endonucleases are chosen to selectively place the newly inserted DNA segments. An aliquot of a reformed vector is then used to transform competent *E. coli* cells by calcium chloride precipitation and selected for recombinant plasmids.

Bacteria are transformed with the plasmid DNA. Luria Broth is inoculated with a bacterial culture and the cells are grown with agitation at optimum temperature to a density of about $10^5$ to $10^7$ cells per ml. The culture is chilled to about 0° C., centrifuged and the cells are collected. The cells are then resuspended in an ice cold sterile solution of 50 mm or calcium chloride and 10 mm tris chloride (pH 8.0). The centrifuge and resuspension step is repeated one more time. The results of the concentrated suspension of treated cells are ready to accept the new vector. Typically the new vector contains a selective marker or reporter gene. Selective marker genes generally encode antibiotic resistance.

For maximum transformation efficiency the bacterial culture preferably is in logarithmic phase of growth; the cell density preferably is low at the time of treatment with calcium chloride; and the treated cells are preferably maintained at 40° C. for 12 to 24 hours. To take up the vector an aliquot of the ligation reaction is added to the suspension of treated cells. The combination is mixed and stored on ice for a short time. Up to 40 nanograms of DNA (dissolved in up to 100 microliters of ligation buffer or TE) can be used for each transformation. Next, the transformed cells and culture tubes are transferred to a 40° C. water bath for 2 minutes. An aliquot of luria broth is added to each tube and the cells incubated at 37° C. for about 30 minutes (tetracycline selection) or 1 hour (ampicillin or kanamycin selection). This period of time allows the bacteria to recover and to begin to express antibiotic resistance. The cells are spread onto selective media and incubated at optimum temperature. Colonies will appear overnight (adapted from Sambrook et al., cited supra.

Transformed *E. coli* are selected through the use of plates containing the appropriate antibiotic (i.e., the one to which resistance is conferred by the introduced plasmid). Typical final concentrations are ampicillin at a 100 micrograms per ml, chlorophenicol at 10 micrograms per ml, kanamycin at 50 micrograms per ml, streptomycin at 25 micrograms per ml, tetracycline at 15 micrograms per ml. When using *E. coli* b121 (DE3) plys as the host, transformants are plated out on a medium containing both ampicillin and chlorophenicol at the above concentrations.

In a preferred embodiment the method for culturing transformed cells can be practiced as described in Sambrook et al., cited supra. Briefly, the method entails transferring of single transformed and selected bacterial colony to a small volume (3 to 5 ml) of bacterial growth medium (such as luria broth) containing an appropriate antibiotic. The culture is incubated at 37° C. (or other appropriate temperature) and scaled up to large volumes.

Cells are lysed with sonication in 830 ml of 50 mm Tris-HCl(pH 7.9)—0.5 mm EDTA containing 100 mm sodium chloride with 10 micrograms per ml of DNASE I. Lysozyme (30 milligrams) is added and the lysate is incubated overnight to disrupt the cell fragments.

To purify recombinant protein from insoluble granules, the lysate is then centrifuged, incubated with sodium deoxycholate, and washed several times. The cell lysate is then frozen and thawed. The cell lysate is further purified by ultrafiltration and DEAE column chromatography. The partially purified fusion protein is then further purified on an affinity column containing sulfanilamide. The partially purified cell lysate is pumped through a column of sulfanilamide-sepharose prepared by conventional methods. The bound protein is washed with 0.5M Tris-sulfate-1M-sodium sulfate (pH 7.5) to remove other materials. The bound multicopy fusion protein containing carbonic anhydrase is eluted with 0.2M potassium thiocyanate and 0.5M-Tris-sulfate (pH 7.5).

The purified multicopy fusion protein is digested with bovine enterokinase in 10 mm tris buffer (pH =8.0) at 37° C. for 15 hours. The enterokinase cleaves at the Asp$_4$Lys interconnecting peptide to form free carbonic anhydrase enzyme and a multicopy fusion protein with a free α-amine group and a C-terminal arginine group. The multicopy peptide is purified from the carbonic anhydrase by ultrafiltration.

The α-amine, ε-amine groups and hydroxyl groups present in the multicopy polypeptide are protected by reaction of the polypeptide with an amine protecting group like maleic anhydride. The maleic anhydride reacts with amines and forms acidic amide protecting groups in the presence of 5M GuHCl (pH 8 to 8.5). This reaction is followed by a buffer exchange by 1 K ultrafiltration.

If the multicopy polypeptide contains carboxyl groups, the β- or γ-carboxyl groups are protected using an activated alcohol like methanol or ethanol. The multicopy polypeptide is then cleaved with trypsin. The trypsin cleaves only at the intraconnecting arginine residues and not at the amine protected lysine residues. The trypsin digestion results in the formation of single copy polypeptides, some of which have free N-terminal amine groups.

The single copy polypeptides are then digested with carboxypeptidase B. The carboxypeptidase B cleaves arginine residues from the C-terminal. If the C-terminal arginine residues are protected at the α-carboxyl group the carboxypeptidase cleaves the ester-protecting group as well as removing the arginine.

The mixture of single copy polypeptides, some having free α-amine groups is treated with maleic anhydride again to protect the free amine groups generated upon cleavage with trypsin. The fully protected single copy polypeptides are then exchanged into a mixture of dimethylformamide and methylene chloride.

The protected polypeptide has protected N-terminal α-amine and an unprotected C-terminal α-carboxyl group generated upon cleavage of the C-terminal arginine. The protected polypeptide is reacted with dicyclohexylcarbodiimide and o-nitrophenol to produce an active ester at the C-terminal α-carboxyl group. The activated protected polypeptide is then transferred to an aqueous solution ammonia to form the amine protected C-terminal α-amide polypeptide.

The protected α-amidated polypeptide amine and hydroxyl groups are deprotected by treatment at a pH of about 2.0 for 2 hours at 20° C. The carboxyl groups are deprotected by alkaline treatment at a pH of about 8 to 10. The deprotected C-terminal α-amide polypeptide is purified by size exclusion chromatography.

EXAMPLE 2

Formation of C-terminal α-Amide Polypeptide from a Recombinant Multicopy Protein Recombinant multicopy protein is formed as described in Example 1. The recombinant multicopy protein has multiple copies of the single copy polypeptide connected with an intraconnecting peptide. The recombinant multicopy polypeptide contains three copies of the myosin light chain kinase inhibitor intraconnected with glutamic acid. The sequence of the myosin light chain kinase inhibitor is Lys-Arg-Arg-Trp-Lys-Lys-Asn-Phe-Ala-Val (SEQ ID NO:9). The DNA sequence encoding the multicopy protein is synthesized by automated methods, and cloned downstream from the T7 promoter in an expression vector prepared as described in Example 1.

The recombinant multicopy protein is expressed in transformed *E. coli* having a recombinant expression vector prepared as described in Example 1. The recombinant multicopy protein is purified from transformed cell lysates by affinity chromatography utilizing an immobilized monoclonal antibody specific for myosin light chain kinase inhibitor.

The multicopy polypeptide is then cleaved with *Staphylococcus aureus* V8 cleavage enzyme at the glutamic acid to form a mixture of multiple units of single copy polypeptides. The mixture of single copy polypeptides also contains polypeptides having unprotected α-amine groups and side chain amine groups generated by the enzyme cleavage of the intraconnecting peptide. These unprotected α-amine groups are protected by reaction with maleic anhydride to form a fully protected single copy peptide having C-terminal glutamic acid residues. The C-terminal glutamic acid residues are removed by carboxypeptidase at pH 4.5.

The removal of the C-terminal glutamic acid and protection of α- and ε-amine groups can be conducted in either order. The fully protected single copy polypeptide is amidated by a reaction with dicyclohexylcarbodiimide in DMF/DCM followed by reaction with ammonium hydroxide. Amidation occurs selectively at the α-carboxyl C-terminal amino acid to form a protected C-terminal α-amide.

The protected C-terminal α-amide of myosin light chain kinase inhibitor is deprotected at pH 2 for about 2 hours. The α-amidated myosin light chain kinase inhibitor is purified by HPLC size exclusion chromatography.

EXAMPLE 3

Formation of C-terminal α-Amide Polypeptide from a Recombinant Single Copy Fusion Protein The recombinant single copy fusion protein is formed as described in Example 1 accept that carbonic anhydrase is connected by an arginine to a single copy of a polypeptide wound healing factor. The sequence of the wound healing factor is Ala-Phe-Ser-Lys-Ala-Phe-Ser-Lys-Ala-Phe-Ser-Lys-Ala-Phe-Ser-Lys-Ala-Phe-Ser-Lys (SEQ ID NO:1). The gene encoding the peptide is produced by automated techniques as described in Example 1 and combined with the gene for the binding protein and the interconnecting peptide in an expression vector as described in Example 1. The single copy fusion protein is expressed and purified as described in Example 1.

The recombinantly produced fusion protein is cleaved at the arginine interconnecting peptide with clostripain to form a single copy polypeptide with an unprotected α-amine group at the N-terminal.

The single copy polypeptide is reacted with maleic anhydride in 5M GuHCl (pH 8 to 8.5) to form a protected single copy polypeptide.

The protected single copy polypeptide is reacted with water soluble carbodiimide in an excess of ammonium hydroxide as an amidating agent to form a protected C-terminal α-amide polypeptide.

The protected C-terminal α-amide polypeptide is deprotected at pH 2 for about 2 hours, and the C-terminal α-amidated wound healing factor is purified by HPLC size exclusion chromatography.

EXAMPLE 4

Selective Modification of the N- and C-terminal Amino Acid α-Carbon Reactive Groups of a Recombinant Polypeptide The recombinant single copy fusion protein is formed as described in Example 3. The single copy fusion protein contains carbonic anhydrase as the binding protein (N-terminal α-amine protecting group) interconnected via the thrombin recognition peptide (Arg-Gly-Pro-Arg) (SEQ ID NO:4) to the wound healing factor with an additional C-terminal arginine residue (C-terminal α-carboxyl protecting group). The single copy polypeptide is protected at both the N- and C-terminal α-carbon reactive groups. The recombinant single copy fusion protein is expressed in a transformed host and purified as described in Example 1.

The recombinant single copy fusion protein is reacted with maleic anhydride in 5M GuHCl(8 to 8.5) to form a protected single copy polypeptide. The maleic anhydride protects the side chain groups of serine and lysine.

The protected single copy fusion protein is then cleaved with thrombin. The thrombin cleaves at the interconnecting peptide to form a protected polypeptide having an unprotected N-terminal α-amine group.

The protected polypeptide with the unprotected N-terminal α-amine group is reacted with a first modifying agent—a pyroglutymal amino acid, in the presence of carbodiimide to form an amide bond between the N-terminal amino acid and a pyroglutymal residue. The reaction is conducted in an organic solvent like DMF to provide solubility of pyroglutymal and carbodiimide. The protected single copy polypeptide is now modified selectively at the N-terminal α-amine reactive group.

The C-terminal arginine is then cleaved off with carboxypeptidase B to form a protected single copy polypeptide modified at the N-terminal α-amine and having an unprotected C-terminal α-carboxyl group. The unprotected C-terminal α-carboxyl group is reacted with a water soluble carbodiimide and excess ammonium hydroxide to form a protected single copy polypeptide with a N-terminal α-amine modified and C-terminal α-carboxyl amide.

The protected single copy polypeptide with the C-terminal α-amide and the N-terminal α-amine pyroglutymal residue is deprotected in an acidic solution at a pH 2 for two hours. After deprotection, the final product is a wound healing factor peptide modified at the C-terminal α-carboxyl by amidation, and modified at the N-terminal α-amine with an additional pyroglutymal residue.

EXAMPLE 5

Replacement of N-terminal Amino Acids of Bradykinin Derived from A Multicopy Fusion Protein The starting material is a multicopy fusion protein containing three copies of a truncated bradykinin peptide interconnected by Asn-Gly to carbonic anhydrase. The carbonic anhydrase gene is obtained and subcloned into the base vector downstream of a T7 promoter as described in Example 1. The gene for the multicopy polypeptide is synthesized by automated synthesis and includes three copies of the coding sequence for amino acid residues 4–9 of bradykinin randomly linked with the coding sequence for Asn connected to the N-terminal of the multicopy polypeptide as follows:

Asn-Gly-Phe-Ser-Pro-Phe-Arg-Gly-Phe-Ser-Pro-Phe-Arg-Gly-Phe-Ser-Pro-Phe-Arg (SEQ ID NO:10)

The Asn-Gly serves as interconnecting peptide cleavable by hydroxylamine. No intraconnecting peptide is necessary as trypsin will cleave at the C-terminal arginine. The gene encoding the multicopy polypeptide with interconnecting peptide is cloned downstream from the carbonic anhydrides as described in Example 1. The vector containing the gene sequence for the recombinant multicopy fusion protein is introduced into a host organism as described in Example 1. The recombinant multicopy fusion protein is expressed and purified, as described in Example 1.

The purified multicopy fusion protein is cleaved with 2M hydroxylamine in 5M GuHCl, pH 8.0 at 37° C. to form a multicopy polypeptide. The multicopy polypeptide is cleaved with trypsin to form a truncated single copy polypeptide with unprotected N-terminal α-amine reactive groups. Optionally, before the cleavage with trypsin, the serine hydroxyl groups can be protected by reaction with maleic anhydride.

The first three amino acids of bradykinin containing a hydroxyproline residue (Hyp) are synthesized by solid phase or solution chemistry. The Arg-Pro-Hyp peptide is synthesized by first forming the 9-fluorenyl methyloxycarbonyl hydroxyproline (FMOC) o-benzylether derivative (FMOC derivative). The FMOC hydroxyproline derivative is reacted with the hydroxide resin to produce FMOC-Hyp-resin. The FMOC is removed with piperidine and DCM (dichloromethane). A dicyclohexylcarbodiimide activated FMOC-proline derivative is then reacted with the resin bound $NH_2$-Hyp. The cycle is repeated for FMOC-Arg-(methoxy-2,3,6-trimethylbenzine sulfonyl). The protected peptide is then cleaved from the resin with 25% trifluoroacetic acid in dichloromethane.

The protected N-terminal tripeptide: Arg-(methoxy-2,3,6 trimethylbenzine sulfonyl)-Pro-Hyp-COOH is activated with dicyclohexyl carbodiimide in dichloromethane and dimethylformamide. The activated peptide is then reacted with a twofold excess of recombinantly produced truncated bradykinin (amino acid residues 4–9) to produce Hyp-3-bradykinin. Excess recombinantly produced bradykinin (amino acids 4–9) can be recovered and used again.

EXAMPLE 6

Formation of N and C-Terminally Modified Growth Hormone Releasing Factor (GRF) Derived From a Multicopy Fusion Protein The starting material is a multicopy fusion protein containing two copies of growth hormone releasing factor intraconnected to form a multicopy polypeptide connected to carbonic anhydrase. The interconnecting peptide and intraconnecting peptide are the same and contain a recognition sequence for an enzymatic cleavage reagent and a recognition sequence for a chemical cleavage reagent. The sequence of the inter- and intraconnecting peptide is:

$Asn_A$-Gly-Pro-$Arg_B$ (SEQ ID NO:11)
A=hydroxylamine cleavage site
B=thrombin cleavage site The gene sequence for the carbonic anhydrase is obtained and subcloned into the base vector downstream of the T7 promoter, as described in Example 1. The gene sequence for growth releasing factor containing the inter- or intraconnecting peptide at the N-terminal end is synthesized by automated oligonucleotide synthesis. The gene sequence with the interconnecting peptide is subcloned immediately downstream from the carbonic anhydrase gene. The gene sequence with the intraconnecting peptide is subcloned immediately downstream from the first copy of the growth releasing factor gene. The Vector is then introduced into a bacterial host and expression of the recombinant multicopy fusion protein is induces as described in Example 1. The recombinant multicopy fusion protein is purified as described in Example 1.

The recombinant multicopy fusion protein is then cleaved with hydroxylamine. Hydroxylamine cleaves at the Asn-Gly recognition sequence in the inter- and intraconnecting peptides to form single copy polypeptides with N-terminal Gly-Pro-Arg peptide and a C-terminal Asn residue.

The single copy polypeptide is then reacted with maleic anhydride to protect ε-amine and hydroxyl groups. The β- and γ-carboxyl groups are protected by formation of o-nitrophenol esters at those groups.

The single copy polypeptide is then cleaved with carboxypeptidase to remove the C-terminal Asn residue. The unprotected C-terminal α-carboxyl group is amidated by the reaction of the protected single copy polypeptide with dicyclohexylcarbodiimide followed by an excess of ammonia.

The single copy polypeptide is then cleaved with thrombin to remove the N-terminal biological protecting group-Gly-Pro-Arg. The unprotected N-terminal α-amine is then reacted with a urethane blocked pyroglutamyl residue to form a protected N-terminally modified, C-terminally modified single copy polypeptide. The terminally modified single copy polypeptide is deprotected at about pH=2 for 2 hours, followed by deprotection at pH=9 for about 2 hours. The final product is growth releasing factor modified at the N-terminal with a pyroglutamyl residue and modified at the C-terminal by amidation.

What is claimed is:

1. A method for selectively modifying a recombinantly produced polypeptide only at a terminal α-carbon reactive group selected from the group consisting of N-terminal α-amine, C-terminal α-carboxyl, and a combination thereof comprising:

modifying the recombinantly produced polypeptide with a biologically added protecting group on one or both terminal α-carbon reactive groups by modifying a DNA sequence encoding the recombinant polypeptide by adding a DNA sequence encoding the biologically added protecting group at the 5' and/or 3' end of the DNA sequence coding for the recombinant polypeptide, wherein the biologically added protecting group is a group that has at least one cleavage sequence that provides for cleavage and removal of the biologically added protecting group and generation of an unprotected terminal reactive α-carbon group on the recombinantly produced polypeptide upon removal, and wherein the recombinantly produced polypeptide has reactive side chain groups selected from the group consisting of ε-amine, hydroxyl, β-carboxyl, γ-carboxyl, thiol, and a combination thereof;

conducting the following reacting and removing steps in any order to produce a side chain protected recombinant polypeptide having at least one unprotected terminal amino acid α-carbon reactive group:

(i) reacting the recombinantly produced polypeptide with up to three chemical protecting agents to selectively protect a reactive side chain group selected from the group consisting of ε-amine, hydroxyl, β-carboxyl, γ-carboxyl, thiol, and a combination thereof;
  (ii) removing the biologically added protecting group with at least one cleavage reagent specific for the biologically added protecting group to form an unprotected terminal amino acid α-carbon reactive group;
modifying the unprotected terminal amino acid α-carbon reactive group with at least one chemical modifying agent to form a terminally modified side chain protected recombinant polypeptide; and
deprotecting the terminally modified side chain protected recombinant polypeptide to form the terminally modified recombinant polypeptide.

2. The method according to claim 1, wherein the recombinantly produced polypeptide is modified with a biologically added protecting group at the N-terminal α-amine reactive group, wherein the biologically added protecting group is a different polypeptide added by an amide bond connection to the N-terminal α-amine reactive group; wherein
  the different polypeptide comprises a binding protein connected to an interconnecting peptide and the interconnecting peptide is the amide bond connection to the recombinantly produced polypeptide and has at least one site cleavable by a chemical or enzymatic reagent, and
  the cleavage reagent specific for the biologically added protecting group is an enzyme that cleaves at the interconnecting peptide, and
  the chemical modifying agent acts to form an acetyl group at the N-terminal α-amine group.

3. The method according to claim 1 wherein: the step of modifying the recombinant peptide includes modifying the recombinantly produced polypeptide by adding a first biologically added protecting group at the N-terminal α-amine group, wherein the first biologically added protecting group comprises a binding protein connected to an interconnecting peptide and the interconnecting peptide is connected to the N-terminal α-amine group and has a cleavage site for a chemical or enzymatic cleavage reagent, and adding a second biologically added protecting group at the C-terminal α-carboxyl group, wherein the second biologically added protecting group is an arginine residue connected to the C-terminal α-carboxyl group;
  the removing step includes removing the first biologically added protecting group with the cleavage reagent specific for the first biologically added protecting group to form a side chain protected recombinant polypeptide having an unprotected N-terminal α-amine;
  the step of modifying the unprotected terminal amino acid α-carbon reactive group includes modifying the unprotected N-terminal α-amine with a first chemical modifying agent to form an N-terminal α-amine modified, side chain protected recombinant polypeptide; and further comprising:
cleaving the second biologically added protective group with a second cleavage reagent specific for the second biologically added protecting group to form an N-terminal α-amine modified, side chain protected recombinant polypeptide with an unprotected C-terminal α-carboxyl group; and
altering the unprotected C-terminal α-carboxyl group with a second modifying agent to form an N-terminal and C-terminal modified side chain protected recombinant polypeptide.

4. The method according to claim 1, wherein the recombinant polypeptide is selected from the group consisting of magainin polypeptide 1, magainin polypeptide 2, magainin polypeptide 3, wound healing peptides, myosin light chain kinase inhibitor, substance P, mastoparan, mastoparan X, human amylin, rat amylin, Icaria chemotactic peptide, carassin, human gastrin releasing peptide, kemptamide, myosin kinase inhibiting peptide, melettin, (leu$^5$)-enkephalamide, (met$^5$)-enkephalamide, metrophenamide, SCP$_B$, allatostatin 1, allatostatin 3, crustacean cardioactive peptide, FMRF (molluscan cardioexcitatory neuropeptide), FMRF-like peptide F1, neuromedian B, bombesin, aleytesin, leukopyrokinin, corazon and littorin.

5. The method according to claim 1, wherein the chemical protecting agent is an agent that selectively protects amine and hydroxyl groups selected from the group consisting of alkyl substituted anhydrates, aryl substituted anhydrates, alkoxy substituted anhydrides, diazo compounds, cyclic anhydrides, alkyl substituted carbamating agents, and aryl substituted carbamating agents.

6. The method according to claim 5, wherein the chemical protecting agent is maleic anhydride.

7. The method of claim 1, wherein the chemical protecting agent is an agent that selectively protects carboxyl groups selected from the group consisting of allyl or benzyl esters, hydrazides, and azides.

8. The method according to claim 7, wherein the chemical protecting agent is o-nitrophenol.

9. The method of claim 1, wherein the chemical protecting agent is an agent that selectively protects a thiol group selected from the group consisting of S-benzyl thioether, S-p-methoxybenzyl thioether, S-p-nitrobenzyl thioether, S-4-picolyl thioether, S-2-picolyl N-oxide thioether, S-9-anthrylmethyl thioether, S-diphenylmethyl thioether, S-Di (p-methoxyphenyl)methyl thioether, S-triphenylmethyl thioether, S-2,4-Dinitrophenyl thioether, S-t-butyl thioether, S-isobutozymethyl hemithioacetal, S-2-tetrahydropyranyl hemithioacetal, S-acetamidomethyl aminothioacetal, S-cyanomethyl thioether, S-2-nitro-1-phenylethyl thioether, S-2,2-Bis(carboethoxy)ethyl thioether, S-benzoyl derivative, S-(N-ethylcarbamate), and S-ethyl disulfide.

10. The method of claim 9, wherein the protecting agent is S-p-methoxybenzyl thioether.

11. The method according to claim 1, wherein the step of deprotecting the terminally modified side chain protected recombinant polypeptide comprises incubating the protected recombinant polypeptide at a pH about 2–4 until substantially all of the protecting groups are removed.

12. The method according to claim 1, wherein in the step of cleaving, the cleavage reagent specific for the biologically added protecting group is selected from the group consisting of enterokinase, factor Xa, thrombin, ubiquitin cleaving enzyme, renin, trypsin, clostripain, S. aureus V8, hydroxylamine, cyanogen bromide, 2-nitro-5-thiocyanobenzoate, amino peptidase, diamino peptidase, carboxyl peptidase, and a combination thereof.

13. A method according to claim 1, wherein the recombinant polypeptide is a multicopy polypeptide having three copies of mastoparan interconnected by arginine residues, and wherein the biologically added protecting group is an arginine added to each C-terminal amino acid of each copy of mastoparan; and wherein the multicopy polypeptide is cleaved with trypsin to generate a single copy polypeptide with unprotected N-terminal a-amine and side chain groups and wherein the single copy polypeptide with unprotected N-terminal α-amine and side chain groups is protected with an amine protecting group, and wherein the C-terminal biologically added protecting group arginine is removed to generate a C-terminal reactive e-carbon group, and wherein the C-terminal α-carbon reactive group is amidated to form a single copy side chain protected C-terminal modified polypeptide, and wherein the single copy side chain protected C-terminal modified polypeptide is deprotected to form a single copy modified recombinant polypeptide.

14. A method according to claim 1, wherein the recombinantly produced polypeptide is growth hormone releasing factor modified at the N-terminal amino acid with a different polypeptide and at the C-terminal amino acid with an Asn-Gly-Pro-Arg (SEQ ID NO:11), wherein the different polypeptide has a binding protein of carbonic anhydrase and an interconnecting peptide Asn-Gly-Pro-Arg (SEQ ID NO:11), wherein the recombinantly produced polypeptide is cleaved with hydroxylamine to yield a single copy polypeptide with an N-terminal Gly-Pro-Arg and a C-terminal Asn as biologically added protecting groups, and wherein single copy polypeptide is protected at ε-amine, β, and γ-carboxyl groups and hydroxyl groups; and wherein the C-terminal biologically added protecting group Asn is removed to generate a C-terminal α-carbon reactive group, and wherein the C-terminal α-carbon reactive group is modified by amidation; and wherein the N-terminal Gly-Pro-Arg biologically added protecting group is removed to generate an N-terminal e-carbon reactive group, and wherein the N-terminal α-carbon reactive group is modified by the addition of a pyroglutamyl residue to yield a single copy N-terminal modified and C-terminal modified protected recombinant polypeptide.

15. A method for selectively modifying a recombinantly produced polypeptide only in a terminal α-carbon reactive group selected from the group consisting of N-terminal α-amine, C-terminal α-carboxyl, and a combination thereof from a recombinantly produced multicopy polypeptide, comprising:

modifying the recombinantly produced multicopy polypeptide with a biologically added protecting group on a terminal α-carbon reactive group on each copy of the recombinant polypeptide by modifying a DNA sequence encoding the recombinant multicopy polypeptide by adding a DNA sequence encoding the biologically added protecting group at the 5' or 3' end of the DNA sequence encoding each copy of the multicopy polypeptide, wherein the biologically added protecting group has at least one cleavage sequence that provides for cleavage and removal of the biologically added protecting group and generation of terminal α-carbon reactive group upon removal, and wherein the recombinant polypeptide includes a ε-amine, hydroxyl, β-carboxyl, γ-carboxyl or thiol reactive side chain group;

conducting the following reacting and removing steps in any order to produce a side chain protected recombinant polypeptide having at least one unprotected terminal amino acid α-carbon reactive group:

reacting the reactive side chain group with a chemical protecting agent to selectively protect the reactive side chain group;

removing the biologically added protecting group with at least one cleavage reagent specific for the biologically added protecting group to form an unprotected terminal amino acid α-carbon reactive group on each copy of the recombinant polypeptide;

modifying the unprotected N-terminal α-amine or C-terminal α-carboxyl group with a chemical modifying agent to form a modified N-terminal α-amine or C-terminal α-carboxyl side chain protected recombinant polypeptide; and deprotecting the N-terminal α-amine modified or C-terminal α-carboxyl side chain protected recombinant polypeptide to form a terminally modified recombinant polypeptide.

16. The method according to claim 15, wherein the recombinant polypeptide is selected from the group consisting of magainin polypeptide 1, magainin polypeptide 2, magainin polypeptide 3, wound healing peptides, myosin light chain kinase inhibitor, substance P, mastoparan, mastoparan X, human amylin, rat amylin, Icaria chemotactic peptide, carassin, human gastrin releasing peptide, kemptamide, myosin kinase inhibiting peptide, melettin, (leu$^5$)-enkephalamide, (met$^5$)-enkephalamide, metrophenamide, SCP$_B$, allatostatin 1, allatostatin 3, crustacean cardioactive peptide, FMRF (molluscan cardioexcitatory neuropeptide), FMRF-like peptide F1, neuromedian B, bombesin, aleytesin, leukopyrokinin, corazon and littorin.

17. The method of claim 1 wherein the chemical modifying agent includes (i) a carbodiimide, an acid chloride, a mixed anhydride, an azide, o-nitrophenol, or 1-hydroxybenzotriazole, and (ii) ammonia.

* * * * *

UNITED STATES PATENT AND TRADEMARK OFFICE
CERTIFICATE OF CORRECTION

PATENT NO. : 5,635,371

DATED : June 3, 1997

INVENTOR(S) : Stout et al.

It is certified that error appears in the above-identified patent and that said Letters Patent is hereby corrected as shown below:

Col. 49, line 2, claim 13: "e-carbon" should read --$\alpha$-carbon--

Col. 49, line 26, claim 14: "e-carbon" should read --$\alpha$-carbon--

Signed and Sealed this

Second Day of December, 1997

BRUCE LEHMAN

*Attest:*

*Attesting Officer*  *Commissioner of Patents and Trademarks*